(12) United States Patent
Li et al.

(10) Patent No.: US 10,316,327 B2
(45) Date of Patent: Jun. 11, 2019

(54) GENETICALLY MODIFIED PLANTS THAT ARE INSECT-RESISTANT AND/OR ROT RESISTANT

(71) Applicants: Yi Li, Mansfield, CT (US); Lisa Hollister, New Richmond, OH (US)

(72) Inventors: Yi Li, Mansfield, CT (US); Lisa Hollister, New Richmond, OH (US)

(*) Notice: Subject to any disclaimer, the term of this patent is extended or adjusted under 35 U.S.C. 154(b) by 0 days.

(21) Appl. No.: 14/212,380

(22) Filed: Mar. 14, 2014

(65) Prior Publication Data
US 2014/0283221 A1 Sep. 18, 2014

Related U.S. Application Data

(60) Provisional application No. 61/862,148, filed on Aug. 5, 2013, provisional application No. 61/787,412, filed on Mar. 15, 2013.

(51) Int. Cl.
*C12N 15/82* (2006.01)
(52) U.S. Cl.
CPC ..... *C12N 15/8282* (2013.01); *C12N 15/8286* (2013.01); *Y02A 40/162* (2018.01)
(58) Field of Classification Search
CPC .. C12N 15/8286; Y02A 40/162; A01N 65/00; C07K 14/42
See application file for complete search history.

(56) References Cited

U.S. PATENT DOCUMENTS

| | | | |
|---|---|---|---|
| 5,407,454 A | 4/1995 | Cavalieri et al. | |
| 5,545,820 A | 8/1996 | Gatehouse et al. | |
| 6,025,542 A | 2/2000 | Smeekens et al. | |
| 6,703,539 B1 | 3/2004 | Keller et al. | |
| 7,105,650 B2 | 9/2006 | Adler | |
| PP18,904 P2 | 6/2008 | Core | |
| 7,390,937 B2 | 6/2008 | Good et al. | |
| 7,629,440 B2 | 12/2009 | Segal et al. | |
| 7,968,693 B2 | 6/2011 | Adler | |
| 8,034,997 B2 | 10/2011 | Bogdanova et al. | |
| 2003/0157592 A1 | 8/2003 | Lerchl et al. | |
| 2004/0038342 A1 | 2/2004 | Vernekar et al. | |
| 2004/0236082 A1 | 11/2004 | Marshall et al. | |
| 2006/0014936 A1* | 1/2006 | Malvar | C07K 14/325 530/387.1 |
| 2006/0162006 A9 | 7/2006 | Sherman et al. | |
| 2006/0224327 A1 | 10/2006 | Dunlap | |
| 2007/0067876 A1 | 3/2007 | Smith et al. | |
| 2008/0163395 A1 | 7/2008 | Song et al. | |
| 2009/0031457 A1 | 1/2009 | Howe et al. | |
| 2009/0300790 A1 | 12/2009 | Aharoni et al. | |
| 2013/0150599 A1 | 6/2013 | Walsh et al. | |

FOREIGN PATENT DOCUMENTS

| WO | 0027876 A1 | 5/2000 |
|---|---|---|
| WO | 2000055328 A1 | 9/2000 |

OTHER PUBLICATIONS

Vandenborre et al, Phytochemistry (2011) 72: 1538-1550.*
Van Damme et al, Plant Physiol. (1995) 107: 833-843.*
Chen et al, Annu. Rev. Entomol. (2011) 56:81-101.*
Tazaki, Kiyoshi, et al. Expression of cDNA for a bark lectin of Robinia in transgenic tobacco plants. FEBS letters 377.1 (1995): 54-58.*
Mazur, Barbara J., and Chok-Fun Chui. "Sequence of a genomic DNA clone for the small subunit of ribulose bis-phosphate carboxylase-oxygenase from tobacco." Nucleic acids research 13.7 (1985): 2373-2386.*
Van Damme, Els JM, et al. "The bark of Robinia pseudoacacia contains a complex mixture of lectins (characterization of the proteins and the cDNA clones)." Plant physiology 107.3 (1995): 833-843.*
Samac, Deborah A., et al. "A comparison of constitutive promoters for expression of transgenes in alfalfa (*Medicago sativa*)." Transgenic research 13.4 (2004): 349-361.*
Khoudi et al (2006) GenBank accession X96847.*
Wong et al, Plant Molecular Biology (1992) 20:81-93.*
Sá et al, International Biodeterioration & Biodegradation (2008) 62: 460-464.*
Feys et al, Trends in Genetics (2000) 16: 449-455.*
Hudson et al (Plant Physiology (2003) 133: 1605-1616).*
Khoudi, Habib, et al. "An alfalfa rubisco small subunit homologue shares cis-acting elements with the regulatory sequences of the RbcS-3A gene from pea." Gene 197.1 (1997): 343-351.*
Wong, Edith Y., Catherine M. Hironaka, and David A. Fischhoff. "*Arabidopsis thaliana* small subunit leader and transit peptide enhance the expression ofBacillus thuringiensis proteins in transgenic plants." Plant Molecular Biology 20.1 (1992): 81-93.*
Yoshida, Kazumasa, and Kiyoshi Tazaki. "Expression patterns of the genes that encode lectin or lectin-related polypeptides in Robinia pseudoacacia." Functional Plant Biology 26.5 (1999): 495-502. (Year: 1999).*
Tazaki, Kiyoshi, et al. "Expression of cDNA for a bark lectin of Robinia in transgenic tobacco plants." FEBS letters 377.1 (1995): 54-58. (Year: 1995).*
Van Damme, Els JM, et al. "The bark of Robinia pseudoacacia contains a complex mixture of lectins (characterization of the proteins and the cDNA clones)." Plant physiology 107.3 (1995): 833-843. (Year: 1995).*
Khoudi, Habib, et al. "An alfalfa rubisco small subunit homologue shares cis-acting elements with the regulatory sequences of the RbcS-3A gene from pea." Gene 197.1 (1997): 343-351. (Year: 1997).*
Samac, Deborah A., et al. "A comparison of constitutive promoters for expression of transgenes in alfalfa (*Medicago sativa*)." Transgenic research 13.4 (2004): 349-361. (Year: 2004).*

(Continued)

*Primary Examiner* — Weihua Fan
(74) *Attorney, Agent, or Firm* — Wood Herron & Evans LLP

(57) ABSTRACT

An insect-resistant and/or fungi-resistant transgenic plant. The plant may be transformed with a gene construct including at least one gene chosen from LECRPA1, LECRPA2, and LECRPA3.

10 Claims, 12 Drawing Sheets
(7 of 12 Drawing Sheet(s) Filed in Color)
Specification includes a Sequence Listing.

(56) References Cited

OTHER PUBLICATIONS

Wong, Edith Y., Catherine M. Hironaka, and David A. Fischhoff. "*Arabidopsis thaliana* small subunit leader and transit peptide enhance the expression ofBacillus thuringiensis proteins in transgenic plants." Plant molecular biology 20.1 (1992): 81-93. (Year: 1992).*
Peumans, Willy J., and E. J. Van Damme. "Lectins as plant defense proteins." Plant physiology 109.2 (1995): 347-352. (Year: 1995 ).*
Vandenborre, Gianni, Guy Smagghe, and Els JM Van Damme. "Plant lectins as defense proteins against phytophagous insects." Phytochemistry 72.13 (2011): 1538-1550. (Year: 2011).*
Tazaki, Kiyoshi, et al. "Expression of cDNA for a bark lectin of Robinia in transgenic tobacco plants." FEBS letters 377.1 (1995): 54-58. (Year: 1995).*
Van Damme, Els JM, et al. "The bark of Robinia pseudoacacia contains a complex mixture of lectins (characterization of the proteins and the cDNA clones)." Plant physiology 107.3 (1995): 833-843. (Year: 1995).*
Partial Search Report/Invitation to Pay Additional Fees in corresponding International Patent Application No. PCT/US2014/028435, dated Jul. 3, 2014, 3 pgs.
Van Damme, E.J.M. et al., "The Bark of Robinia pseudoacacia Contains a Complex Mixture of Lectins, Characterization of the Proteins and the cDNA Clones," Plant Physiol. (1995) 107:833-843.
De Araujo, R.M.S. et al., "Crataeva tapia bark lectin is an affinity adsorbent and insecticidal agent," Plant Science (2012) 183:20-26.
GenBank_U12782, Robinia pseudoacacia clone LECRPA1 lectin mRNA, complete eds, Oct. 31, 1995, [online]. [Retrieved on Jun. 30, 2014]. Retrieved from the Internet: <URL: http://www.ncbi.nlm.nih.gov/nuccore/U12782><http://www.ncbi.nlm.nih.gov/nuccore/U12782> Reference, Title, Journal, and Origin.
International Search Report and Written Opinion in International Patent Application No. PCT/US2014/028435, dated Sep. 25, 2014, 18 pgs.
International Search Report and Written Opinion in International Patent Application No. PCT/US2014/028546, dated Dec. 9, 2014, 14 pgs.
Tazaki, K. et al., "Expression of cDNA for a bark lectin of Robinia in transgenic tobacco plants," FEBS Letters (1995) 377:54-58.
International Preliminary Report on Patentability dated Sep. 15, 2015 in International Application No. PCT/US2014/028435, 11 pgs.
International Preliminary Report on Patentability dated Sep. 15, 2015 in International Application No. PCT/US2014/028546,9 pgs.
(Author unknown) "Deer eating away at forests nationwide," (2005) www.msnbc.msn.com/id/6835501/ns/us_news-environment/t/deer-eating-away-forests-nationwide, 2 pgs.
(Author unknown) "Genetically Engineered Trees: Promise and Concerns," Resources for the Future (2011), www.rff.org/News/Features/Pages/Genetically-Engineered-Trees.aspx., 1 pg.
(Author unknown), "Crops Designed to Grow Drugs Spark New Debate Over Rules," www.livestockweekly.com/papers/03/11/06/whlpharmacrops.asp, (2011) 3 pgs.
(Author unknown), "PCT: Genes and Bitter Taste," http://learn.genetics.utah.edu/content/begin/traits/ptc (2011) 3 pgs.
Ahmed, I. et al., "High-quality plant DNA extraction for PCR: an easy approach," Journal of Applied Genetics (2009) 50(2):105-107.
Betley, M.J. et al., "Nucleotide Sequence of the Type A Staphylococcal Enterotoxin Gene," Journal of Bacteriology (1988) 170(1):34-41.
Byrne, P., "Bio-pharming," Crop Series Production (2003) Fact Sheet No. 0.307, 6 pgs.
Cardoza, V. et al., "Increased Agrobacterium-mediated transformation and rooting efficiencies in canola (*Brassica napus* L.) from hypocotyl segment explants," Plant Cell Rep. (2003) 21:599-604.
Chen, X. et al., "A survey of quantitative real-time polymerase chain reaction internal reference genes for expression studies in *Brassica napus*," Analytical Biochemistry (2010) 405:138-140.

Chen, Y. et al., "In vitro regeneration and Agrobacterium-mediated genetic transformation of Euonymus alatus," Plant Cell Reports (2006) 25(10):1043-1051.
Clough, S.J. et al., "Floral dip: a simplified method for Agrobacterium-mediated transformation of *Arabidopsis thaliana*," Plant J. (1998) 16(6):735-743.
Conover, M.R., "Monetary and intangible valuation of deer in the United States," Wildl. Soc. Bull. (1997) 25(2):298-305.
Cseke, L.J. et al., "High efficiency poplar transformation," Plant Cell Rep. (2007) 26:1529-1538.
Eckhardt, N.A., "Moco Mojo: Crystal Structure Reveals Essential Features of Eukaryotic Assimilatory Nitrate Reduction," The Plant Cell (2005) 17:1029-1031.
Helenius, E. et al., "Gene Delivery into Intact Plants Using the Helios™ Gene Gun," Plant Molecular Biology Reporter (2000) 18:287a-2871.
Hennekinne, J.A. et al., "*Staphylococcus aureus* and its food poisoning toxins: characterization and outbreak investigation," FEMS Microbiol. Rev. (2012) 36:815-836.
Horton, P., "Prospects for crop improvement through the genetic manipulation of photosynthesis: morphological and biochemical aspects of light capture," J. Exp. Bot. (2000) 51(suppl 1):475-485.
Khoudi, H. et al., "An alfalfa rubisco small subunit homologue shares cis-acting elements with the regulatory sequence of the RbcS-3A gene from pea," Gene (1997) 197:343-351.
Kim, S. et. al., "*Arabidopsis thaliana* Rubisco small subunit transit peptide increases the accumulation of Thermotoga maritima endoglucanase Cel5A in chloroplasts of transgenic tobacco plants," Transgenic Res. (2010) 19:489-497.
Labra, M. et al., "Genomic stability in *Arabidopsis thaliana* transgenic plants obtained by floral dip," Theor. Appl. Genet. (2004) 109:1512-1518.
Lemaux, P.G., "Genetically Engineered Plants and Foods: A Scientist's Analysis of the Issues (Part I)," Annu. Rev. Plant Biol. (2008) 59:771-812.
Maheshwari, P. et al., "Optimization of *Brassica napus* (canola) explant regeneration for genetic transformation," New Biotechnology (2011) 29(1)144-156.
Marvier, M., "Pharmaceutical crops have a mixed outlook in California," California Agriculture (2007) 61(2):59-66.
Rabijns, A. et al., "Structure of a Legume Lectin From the Bark of Robinia pseudoacacia and Its Complex With N-Acetylgalactosamine," Proteins Struct. Funct. Genet. (2001) 44:470-478.
Roh, J.Y. et al., "Bacillus thuringiensis as a Specific, Safe, and Effective Tool for Insect Pest Control," J. Microbiol. Biotechnol. (2007) 17(4):547-559.
Sa, R.A. et al., "Induction of mortality on Nasutitermes corniger (Isoptera, Termitidae) by Myracrodruon urundeuva heartwood lectin," International Biodeterioration & Biodegradation (2008) 62:460-464.
Shama, L.M. et al., "The Benefits and Risks of Producing Pharmaceutical Proteins in Plants," Risk Management Matters (2004) 2(4):28-33.
Sinclair, T.R. et al., "Crop transformation and the challenge to increase yield potential," Trends in Plant Science (2004) 9(2):70-75.
Soegaard, B., "Breeding for resistance to insect attack in forest trees," www.fao.org/docrep/03650e/03650e09.htm, 13 pgs.
Strauss, S.H. et al., "Genetically modified poplars in context," The Forestry Chronicle (2001) 77(2):271-279.
Voosen, P., "Genetically Modified Forest Planned for U.S. Southeast," Scientific American (online) (2010), 2 pgs.
Yang, J. et al., "Seasonal changes in gene expression at the sapwood-heartwood transition zone of black locust (*Robinia pseudoacacia*) revealed by cDNA microarray analysis," Tree Physiology (2004) 24:461-474.
Guo, H.H. et al. (Protein tolerance to random amino acid change, Proc. Natl. Acad. Sci. USA 101:9205-9210, 2004).
Hill, M.A. et al. (Functional analysis of conserved histidines in ADP-glucose pyrophosphorylase from *Escherichia coli*. Biochem. Biophys. Res. Comm. 244:573-577, 1998).
Office Action in U.S. Appl. No. 14/212,834, dated Sep. 29, 2016, 54 pgs.

(56) References Cited

OTHER PUBLICATIONS

Pinchuk, I.V. et al. (Staphylococcal Enterotoxins. Toxins, 2, 2177-2197, 2010).
Shimamura, Y. et al. (Plant-Derived Polyphenols Interact with Staphylococcal Enterotoxin A and Inhibit Toxin Activity. PLOS ONE. p. 1-13, Jun. 7, 2016).
Vasconcelos, I.M. et al. (Review. Antinutritional properties of plant lectins. Toxicon 44: 385-403, 2004).

* cited by examiner

Verification of construct pRBSK-1A-RS-LECRPA1-2-3-tNOS
Lane M:Marker; Lane1,4:LECRPA1 gene(858bp);
Lane2,5:LECRPA2 gene (861bp); Lane3,6:LECRPA2 gene (783bp)

GENETICALLY MODIFIED PLANTS THAT ARE INSECT-RESISTANT AND/OR ROT RESISTANT

CROSS-REFERENCE TO RELATED APPLICATIONS

This application claims priority to, and the benefit of the filing date of, U.S. Provisional Patent Application No. 61/787,412, filed on Mar. 15, 2013, entitled "Genetically Modified Plants that are Insect-Resistant and/or Rot-Resistant," and U.S. Provisional Patent Application No. 61/862,148, filed on Aug. 5, 2013, entitled "Genetically Modified Plants that are Animal-Resistant, Insect-Resistant, and/or Rot-Resistant," the disclosures of which are incorporated by reference herein in their entireties.

FIELD OF THE INVENTION

This invention relates to methods for imparting insect resistance and rot resistance to plants, and to woody tissues of plants.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Termites are eusocial insects that live in colonies that may number from several hundred to several million. Due to their wood-eating habits, many termite species can do great damage to unprotected buildings and other wooden structures. Their habit of remaining concealed often results in their presence being undetected until timbers are severely damaged and exhibit surface changes. Once termites have entered a building, they do not limit themselves to wood; they also damage paper, cloth, carpets, and other cellulosic materials.

Every year, large amounts of damage are done to homes, businesses, and other structures due to the eating habits of termites. As such, termites are commonly viewed as severe pests in many countries, because of the damage they can cause to structures and similar nuisances. Large amounts of money are spent every year on procedures (often involving harsh chemicals, e.g., insecticides) to prevent termite damage.

Apart from termites, wood structures (such as wood found in homes, businesses, and other structures) are also susceptible to rot. Often, rot is caused by one or more fungi. For example, a wood-decay fungus is a variety of fungus that digests moist wood, causing it to rot. Some wood-decay fungi attack dead wood, such as brown rot, and some are parasitic and colonize living trees. Various fungi consume wood in various ways. For example, some attack the carbohydrates in wood, and some others decay lignin. Wood-decay fungi can be classified according to the type of decay that they cause. The best-known types are brown rot, soft rot, and white rot. Different types of fungi cause these different types of rot: white-rot (*Phanerochaete chrysosporium*), brown-rot (*Gloeophyllum trabeum*), and soft-rot (*Trichoderma reesei*).

Unfortunately, currently there are no effective methods available for preventing damage to wood from termites (in the absence of the use of substances such as harsh chemicals) or rot that cause huge monetary losses to both plant related industries and the end users.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

As described above, there are numerous problems with damage and destruction of wood due to insects (such as termites) and rot (such as is caused by fungi) resulting in large costs to homeowners and others.

However, there are a number of plants that are toxic to insects and/or fungi and therefore resistant to termites and fungi (organisms that consume wood and rot wood). For example, the black locust tree (which can be found throughout the eastern United States and south-eastern Canada bearing sweet-smelling clusters of white flowers) is resistant to insects and fungi because it contains toxin proteins called lectins.

Biochemical and molecular studies have demonstrated that black locust tissues, such as bark, express three genes encoding three different lectin polypeptides. One of these genes encodes lectin polypeptide C (26 kDa) that associates exclusively into homotetramers [called *Robinia pseudoacacia* bark agglutinin II or RPbAII (see vanDamme E J M, Barre A, Smeets K, Torrekens S, van Leuven F, Rouge P, Peumans W J (1995): The bark of *Robinia pseudoacacia* contains a complex mixture of lectins. Characterization of the proteins and the cDNA clones. Plant Physiol 107:833-843), incorporated by reference herein in its entirety]. Two other genes encode lectin polypeptides A and B (31.5 and 29 kDa, respectively), which associate in all possible combinations into five different tetramericisolectins. The mixture of these five isoforms is called *Robinia pseudoacacia* bark agglutinin I (RPbAI) [Rabijns, A., C. Verboven, P. Rougé, A. Barre, E. J. M. Van Damme, W. J. Peumans and C. J. De Ranter (2001): Proteins Struct. Funct. Genet, 44: 470-478, incorporated by reference herein in its entirety].

Black locust wood is resistant to termite and decay, which is likely explained by the fact that the plant produces the RPbAI proteins. Lectins were detected in *Myracrodruon urundeuva*, a termite-resistant heartwood as well [Sá, R. A T. H. Napoleão, N. D. L. Santos, F. S. Gomes, A. C. Albuquerque, H. S. Xavier, L. C. B. B. Coelho, L. W. Bieber and P. M. G. Paiva, (2008): Induction of mortality on *Nasutitermes corniger* (Isoptera, Termitidae) by *Myracrodruon urundeuva* heartwood lectin. International Biodeterioration and Biodegradation 62: 460-464]. Sa et al (2008) further showed that lectins have strong toxic effect on termites. This suggests that RPbAI and RPbAII play a key role in protecting black locust against termites and fungi.

Thus, one aspect of the present invention provides for construction of a fusion gene for the three genes from RPbAI (polypeptides A and B) and RPbAII (polypeptide C) from black locust. Another aspect of the present invention provides for a genetically modified plant including these genes. Such plants will then express the toxic lectin proteins, thereby imparting insect resistance and fungal resistance to the plant. The proteins may be stored in the endoplasmic reticulum membranes (ERs) or vacuoles of plant leaves, bark, shoot and root tissues.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE INVENTION

Figure 1:
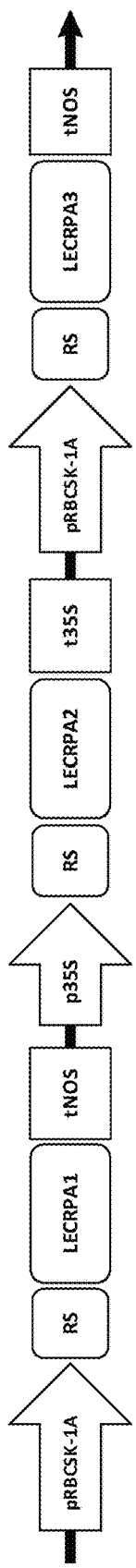
FIG. 1 is a schematic illustrating a gene construct including the LECRPA1, LECRPA2, and LECRPA3 genes (a LECRPA1+2+3 construct). As will be described below, LECRPA1, LECRPA2, and LECRPA3 (as used herein) are cDNA clones that can be isolated from a cDNA library to obtain three classes of lectin cDNA clones corresponding to the a and b polypeptides of RPbAI and the c polypeptide of RPbAII.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described above in the Summary, there are a number of plants that are toxic to insects and/or fungi and therefore resistant to termites and fungi (organisms that consume wood and rot wood). For example, the black locust tree (which can be found throughout the eastern United States and south-eastern Canada bearing sweet-smelling clusters of white flowers) is resistant to insects and fungi because it contains toxin proteins called lectins.

Biochemical and molecular studies have demonstrated that black locust tissues, such as bark, express three genes encoding three different lectin polypeptides. One of these genes encodes lectin polypeptide C (26 kDa) that associates exclusively into homotetramers [called *Robinia pseudoacacia* bark agglutinin II or RPbAII (see vanDamme E J M, Barre A, Smeets K, Torrekens S, van Leuven F, Rouge P, Peumans W J (1995): The bark of *Robinia pseudoacacia* contains a complex mixture of lectins. Characterization of the proteins and the cDNA clones. Plant Physiol 107:833-843, incorporated by reference herein in its entirety]. Two other genes encode lectin polypeptides A and B (31.5 and 29 kDa, respectively), which associate in all possible combinations into five different tetramericisolectins. The mixture of these five isoforms is called *Robinia pseudoacacia* bark agglutinin I (RPbAI) [Rabijns, A., C. Verboven, P. Rouge, A. Barre, E. J. M. Van Damme, W. J. Peumans and C. J. De Ranter (2001): Proteins Struct. Funct. Genet, 44: 470-478, incorporated by reference herein in its entirety].

As described above, it has been determined that certain lectins have potent toxic activity against insects and fungi. Thus, one aspect of the present invention provides a method for preparing termite-resistant and rot-resistant wood, by creating a genetically modified plant (e.g., a woody plant) that expresses proteins encoded by the RPbAI and RPbAII genes.

As is known to those of ordinary skill in the art, there are multiple ways to obtain the desired DNA sequences for the present invention, and to transform plants therewith. For example, the DNA sequences which code for the lectins of this invention can be obtained by conventional techniques, which are well known to (and routinely used by) those of ordinary skill in the art. For example, the lectin can be sequenced in its entirety, using known methods, and synthetic DNA sequences can then be prepared which code for the appropriate sequence of amino acids, and this synthetic sequence can be inserted into an appropriate plant expression cassette. Such techniques are applicable to any gene that is useful in imparting insect or fungal resistance, such as each of the genes (e.g., lectin genes) identified herein. For example, such techniques may be used with (but not limited to) the LECRPA1, LECRPA2, and/or LECRPA3 genes.

Likewise, numerous plant expression cassettes and vectors are well known in the art. By the term "expression cassette" is meant a complete set of control sequences including initiation, promoter and termination sequences which function in a plant cell when they flank a structural gene in the proper reading frame. Expression cassettes frequently and preferably contain an assortment of restriction sites suitable for cleavage and insertion of any desired structural gene. The cloned gene will have a start codon in the correct reading frame for the structural sequence. In addition, the plant expression cassette preferably includes a strong constitutive promoter sequence at one end to cause the gene to be transcribed at a high frequency, and a poly-A recognition sequence at the other end for proper processing and transport of the messenger RNA. Plant expression cassettes can be designed to include one or more selectable marker genes.

It will also be appreciated by those of ordinary skill that the plant vectors provided herein can be incorporated into *Agrobacterium tumefaciens*, which can then be used to transfer the genes of interest into susceptible plant cells. Thus, one example for transforming plants includes a method for imparting insect resistance and/or rot resistance in *Agrobacterium tumefaciens*-susceptible plants in which the expression cassette is introduced into the cells by infecting the cells with *Agrobacterium tumefaciens*, a plasmid of which has been modified to include a plant expression cassette (such as is described above). *Agrobacterium* mediated plant transformation methods are well known to those skilled in the art. However, other methods of transforming plants are well known to those of ordinary skill in the art—and such other methods may be alternatively used to transform plants to impart such insect resistance and/or rot resistance. For example, other aspects of the present invention include a method for imparting insect resistance and/or rot resistance in any plant species using a gene gun or other physical or chemical methods for gene delivery (e.g., that described in Helenius, Elina; Boije, Maria; Niklander-Teeri, Viola; Palva, E. Tapio; Heeri, Teemu U. "Gene Delivery Into Intact Plants Using the Helios Gene Gun". Plant Molecular Biology Reporter; 2000, 18: 287a-2871, incorporated by reference herein in its entirety).

Thus, one embodiment of the present invention includes cloning and sequencing all cDNA and genomic DNA sequences of the three RPbAI/RPbAII genes from black locust. The genomic DNA of the three genes should contain their promoter, coding and 3'-termination sequences. The cDNA and genomic DNA sequences can then be modified to make them suitable for high expression in leaf, bark, shoot and root organs. Multiple sets of fusion genes may be constructed. For example, one such set may include the three native black locust genes, using their native promoter and 3'-termination sequences. Another such set may use an Alfalfa RbcS gene promoter sequence to control the expression of the coding sequences of the three black locust gene. It will be recognized by those of ordinary skill in the art that other genes of interest may be used, as well as other gene promoter sequences (e.g., 35S CaMV gene promoter sequence). An example of such a fusion gene construct is shown schematically in FIG. 1.

In one embodiment, multiple cDNA clones can be isolated from a cDNA library to obtain three classes of lectin cDNA clones corresponding to the a and b polypeptides of RPbAI and the c polypeptide of RPbAII. These cDNA clones are referred to as LECRPA1, LECRPA2, and LECRPA3.

Thus, in various embodiments of the present invention, the gene construct includes LECRPA1, LECRPA2, or LECRPA3, or any combination of such lectins. The lectin can be incorporated into the tissues of a susceptible plant so that in the course of infesting the plant, the insect (e.g., termite) or fungus encounter insecticidal or fungicidal amounts of the selected lectin or lectins. (While this embodiment and other embodiments herein—refer to an insecticidal or fungicidal effect of the genetically modified plants of the various aspects of the present invention, other embodiments may impart a resistance that is not completely insecticidal or fungicidal, but still imparts a resistance that reduces the insect or fungal effect. And so "insecticidal" and "fungicidal" may be read as incorporating both kinds of resistance.) Since the genes that code for these lectins can be isolated, cloned, inserted into an appropriate expression cassette, and introduced into cells of any plant species, one embodiment of the method involves inserting into the genome of a plant a DNA sequence coding for one or more insecticidal and/or fungicidal plant lectins in proper reading frame relative to transcription initiator and promoter sequences inserted with the genes (or active in the plant). Transcription and translation of the DNA sequence causes expression of the lectin protein sequence at levels which provide an insecticidal and/or fungicidal amount of the lectin in the tissues of the plant which are normally infested or consumed by the insect (e.g., termite) and/or fungus.

LECRPA1, contains an 856-bp open reading frame encoding a 285-amino acid precursor with one possible initiation codon at position 1 of the deduced amino acid sequence. Translation starting with this Met residue results in a lectin precursor with a calculated molecular mass of 30,928 D, which after co-translational cleavage of the signal peptide of 31 amino acids yields a lectin precursor polypeptide of 27,330 D with an N-terminal amino acid sequence identical to the one determined for the a polypeptide of RPbAI.

The estimated pI for the lectin polypeptide encoded by LECRPA1 is 5.04. The deduced amino acid sequence of the lectin cDNA clone LECRPA1 contains two putative glycosylation sites at positions 147 and 188. (See Van Damme E J M, Barre A, Smeets K, Torrekens S, Van Leuven F, Rouge P, Peumans W J (1995b) The bark of *Robinia pseudoacacia* contains a complex mixture of lectins. Plant Physiol 107: 833-843, incorporated by reference herein in its entirety.)

The following is the gene sequence of LECRPA1 [GenBank: U12782.1, 858 bp]:

[SEQ. ID. NO. 1]
ATGACTTCCTACAACTTCAAAACCCAAACCTCCTTCCCTCTTCTCCTATC

CATATCCTTTTTTTCCTCTTGTTACTCAACAAGGTGAATTCAACTGGAT

CTCTCTCCTTTTCTTTCCCCAAGTTCGCGCCTAACCAACCATATCTGATC

TTCCAACGTGATGCCCTTGTGACATCAACAGGGGTGTTACAACTCACCAA

CGTAGTTAACGGGGTACCATCCGGTAAATCTCTTGGTAGAGCTCTATATG

CTGCCCCTTTCCAAATCTGGGATAGCACCACAGGCAACGTGGCTAGCTTT

GTCACTTCCTTCTCCTTTATCATTCAAGCACCTAACCCAACCACAACGGC

AGATGGTCTTGCCTTCTTTCTTGCACCAGTTGATACTCAGCCCTTAGATG

TTGGAGGAATGCTCGGAATTTTCAAAGACGGATATTTCAATAAATCCAAC

CAAATTGTTGCAGTTGAATTCGATACCTTTTCAAATATTCACTTTGATCC

AAAAGGTAGACATATGGGAATCAATGTCAACTCCATCGTGTCCATAAAAA

CCGTGCCATGGAATTGGACAAATGGCGAAGTAGCCAATGTTTTCATAAGC

TATGAAGCTTCCACCAAATCCTTAACTGCCTCTTTTGGTTTATCCTTCACT

TGAAACAAGTTTTATCGTTCATGCTATTGTGGATGTGAAGGATGTTCTTC

CCGAGTGGGTAAGATTTGGTTTCTCAGCTACCACAGGAATAGATAAAGGC

TACGTTCAAACAAATGATGTTCTCTCCTGGTCTTTCGAGTCAAACTTGCC

AGGTGGTAACAGTGTTGCTTCGGTGAAGAACGCGGGTCTTTCAACCTATG

CTGCATGA.

And the amino acid sequence of LECRPA1 is:

[SEQ. ID. NO. 2]
MTSYNFKTQTSFPLLLSISFFFLLLLNKVNSTGSLSFSFPKFAPNQPYLI

FQRDALVTSTGVLQLTNVVNGVPSGKSLGRALYAAPFQIWDSTTGNVASF

VTSFSFIIQAPNPTTTADGLAFFLAPVDTQPLDVGGMLGIFKDGYFNKSN

QIVAVEFDTFSNIHFDPKGRHMGINVNSIVSIKTVPWNWTNGEVANVFIS

YEASTKSLTASLVYPSLETSFIVHAIVDVKDVLPEWVRFGFSATTGIDKG

YVQTNDVLSWSFESNLPGGNSVASVKNAGLSTYAA

LECRPA2 encodes a 286-amino acid precursor with a calculated molecular mass of 31,211 D, which after cleavage of the signal peptide, 31 amino acids, is converted into a 27,600 D lectin polypeptide with an N-terminal amino acid sequence similar to the one determined for the b polypeptide of RPbAI and an estimated pI of 4.95. The sequence of this lectin polypeptide contains only one putative N-glycosylation site, the position of which coincides with the first possible glycosylation site in LECRPA1. (See Van Damme E J M, Barre A, Smeets K, Torrekens S, Van Leuven F, Rouge P, Peumans W J (1995b) The bark of *Robinia pseudoacacia* contains a complex mixture of lectins. Plant Physiol 107:833-843.)

The nucleic acid sequence of LECRPA-2 [GenBank: U12783.1, 861 bp] is:

[SEQ. ID. NO. 3]
ATGGCTTCCTACAAGTTCAAAACCCAAAACTCCTTCCTTCTTCTCCTATC

CATATCCTTTTTCTTCCTCTTGTTACTCAACAAGGTGAATTCGACTGGAT

CCCTCTCCTTTTCTTTCCCCAAGTTCAAGCATAGCCAACCAGATCTGATC

TTCCAAAGTGATGCCCTTGTGACATCAAAAGGGGTGTTACAACTCACCAC

GGTAAATGATGGAAGACCAGTCTATGACTCTATTGGTCGAGTTCTATATG

CTGCCCCTTTCCAAATTTGGGATAGCACCACTGGCAACGTGGCTAGCTTT

GTCACTTCCTTCTCCTTTATCATCAAAGCACCTAACGAAGGCAAAACGGC

AGATGGTCTTGTCTTCTTTCTTGCACCAGTTGGTAGTACTCAGCCCCTAA

AAGGAGGAGGACTCCTCGGACTTTTCAAAGATGAATCTTACAATAAATCC

AACCAAATTGTTGCAGTTGAATTTGACACATTTCGGAATGTTGCATGGGA

TCCAAATGGAATACATATGGGAATCGATGTCAACTCTATTCAATCCGTAA

GAACTGTGCGATGGGATTGGGCGAATGGCGAAGTAGCCAATGTTTTCATA

AGCTATGAAGCTTCCACCAAATCCTTAACTGCCTCTTTGGTTTATCCTTC

ACTTGAAAAAGTTTTATCTTGAGTGCTATTGTGGATTTGAAGAAAGTTC

TTCCGGAGTGGGTAAGAGTTGGTTTCACAGCTACCACAGGACTATCTGAA

GACTACGTTCAAACAAATGATGTTCTCTCCTGGTCTTTCGAGTCAAACTT

GCCAGGTGGTAACAGTGTTGCTTCGGTGAAGAACGCGGGTCTTTCAACCT

ATGCTGCATGA

And the amino acid sequence of LECRPA2 is:

[SEQ. ID. NO. 4]
MASYKFKTQNSFLLLLSISFFFLLLLNKVNSTGSLSFSFPKFKHSQPDLI

FQSDALVTSKGVLQLTTVNDGRPVYDSIGRVLYAAPFQIWDSTTGNVASF

VTSFSFIIKAPNEGKTADGLVFFLAPVGSTQPLKGGGLLGLFKDESYNKS

NQIVAVEFDTFRNVAWDPNGIHMGIDVNSIQSVRTVRWDWANGEVANVFI

SYEASTKSLTASLVYPSLEKSFILSAIVDLKKVLPEWVRVGFTATTGLSE

DYVQTNDVLSWSFESNLPGGNSVASVKNAGLSTYAA

LECRPA3, encodes a 272-amino acid precursor with one possible initiation site at position 13. Translation starting at this site yields a lectin precursor with a calculated molecular mass of 27,878 D, which after cleavage of the signal peptide, 17 amino acids, is converted into a 25,970 D lectin polypeptide, the N-terminal sequence of which resembles the sequence determined for the c polypeptide of RPbAII.

The estimated pI of the polypeptide encoded by LECRPA3 is 6.5, higher than the pI of the lectin polypeptides encoded by LECRPA1 and LECRPA2. Within the coding sequence of LECRPA3, three putative glycosylation sites are present at positions 36, 39, and 65 of the lectin precursor. (See Van Damme E J M, Barre A, Smeets K, Torrekens S, Van Leuven F, Rouge P, Peumans W J (1995b) The bark of *Robinia pseudoacacia* contains a complex mixture of lectins. Plant Physiol 107:833-843.)

The nucleic acid sequence of LECRPA-3 [GenBank: U12784.1, 783 bp] is:

[SEQ. ID. NO. 5]
ATGCTCATAAGTTTCTTTGTCTTGCTAGCTAGTGCCAGAAAGGAGAACTC

TGATGAAGGAATTTCCTTCAACTTCACCAACTTCACCAGAGGTGATCAAG

GTGTAACCTTACTAGGACAAGCCAACATTATGGCAAATGGGATCTTGGCC

CTCACCAACCATACAAACCCTACTTGGAATACAGGCCGTGCCTTGTATTC

TAAACCAGTTCCTATTTGGGATTCAGCCACTGGCAATGTCGCCAGCTTTG

TTACTTCCTTCTCTTTTGTCGTACAAGAGATCAAAGGTGCTATACCAGCT

GATGGAATTGTTTTCTTCCTTGCACCAGAAGCCAGGATTCCCGACAATTC

AGCCGGTGGGCAACTCGGAATTGTTAATGCCAACAAAGCTTACAATCCAT

TTGTTGGTGTAGAATTTGATACTTACTCCAATAATTGGGATCCTAAATCT

GCACATATTGGAATCGATGCCAGCTCTTTAATTTCATTAAGGACTGTGAA

ATGGAACAAGGTTAGTGGGTCATTGGTCAAAGTTAGTATCATCTATGACT

CTCTATCTAAGACGTTGAGTGTTGTTGTGACTCACGAGAATGGTCAAATT

TCTACCATCGCTCAAGTCGTGGATTTGAAAGCTGTGCTGGGAGAGAAGGT

CAGGGTTGGTTTTACTGCAGCCACCACAACAGGCCGGGAATTATACGACA

TTCATGCATGGTCTTTCACTTCAACTTTGGTGACAGCTACAAGCAGCACC

TCGAAGAACATGAATATTGCAAGCTATGCATGA

And the amino acid sequence of LECRPA3 is:

[SEQ. ID. NO. 6]
MLISFFVLLASARKENSDEGISFNFTNFTRGDQGVTLLGQANIMANGILA

LTNHTNPTWNTGRALYSKPVPIWDSATGNVASFVTSFSFVVQEIKGAIPA

DGIVFFLAPEARIPDNSAGGQLGIVNANKAYNPFVGVEFDTYSNNWDPKS

AHIGIDASSLISLRTVKWNKVSGSLVKVSIIYDSLSKTLSVVVTHENGQI

STIAQVVDLKAVLGEKVRVGFTAATTTGRELYDIHAWSFTSTLVTATSST

SKNMNIASYA

Thus, in one particular embodiment, the gene construct may include LECRPA1, LECRPA2, and LECRPA3 (described above), which is then inserted into the genome of a plant in proper reading frame relative to transcription initiator and promoter sequences. Transcription and translation of the DNA sequence causes expression of the lectin protein sequence at levels which provide an insecticidal and/or fungicidal amount of the lectin in the tissues of the plant which are normally infested or consumed by the insect (e.g., termite) and/or fungus.

As mentioned above, both genomic and cDNA encoding the gene of interest may be used in this invention. When the gene of interest has been isolated, genetic constructs are made which contain the necessary regulatory sequences to provide for efficient expression of the gene in the host cell. According to this invention, the genetic construct will contain (a) at least one genetic sequence coding for a protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

Thus, in one embodiment, the gene constructs of the present invention also include a gene promoter. As is known to those of ordinary skill in the art a gene promoter is a region of DNA that initiates transcription of a particular gene. Promoters are located near the genes they transcribe, on the same strand and upstream on the DNA (towards the 3' region of the anti-sense strand). For transcription to take place, RNA polymerase must attach to the DNA near a gene. Promoters contain specific DNA sequences and response elements that provide an initial binding site for RNA polymerase and for transcription factors that recruit RNA polymerase.

In one embodiment, the gene constructs of the present invention may include the Alfalfa RbcS gene promoter RbcSK-1A. Sequence analysis of the promoter RbcSK-1A shows high sequence homology (80%) to the promoter region of the pea RbcS-3A gene. This homology is limited to 235 bp upstream of the first major putative transcription initiation site determined previously. A G-box like sequence found in the promoters of many genes that respond to a variety of different stimuli is also present in the RbcSK-1A promoter. This box binds trans-acting factors which contain a bZIP motif. Twenty-three base pairs downstream of the G-box, another important element in RbcSK-1A promoter region, known as the I-box, was identified. Many light regulated promoters of both monocots and dicots contain this element. [See Khoudi H, Ve'zina L-P, Mercier J, Castonguay Y, Guy A, Laberge S. (1997) An alfalfa rubisco small subunit homologue shares cis acting elements with the regulatory sequence of the RbcS-3A gene from pea. Gene, 197:343-351, incorporated by reference herein in its entirety.]

The nucleic acid sequence of the Alfalfa RbcS gene promoter RbcSK-1A, GenBank: X96847.1, 1803 bp is:

[SEQ. ID. NO 7]
TCGACCTGCAGGTCAACGGATCAAATGATTCAATATTTGGCTTGATGAAA

TTAGAGAAAATGAAAAATTGGATTTCTAAGTTTGATTGTTATTTTGAGAT

AGAAAAGGAAAAATCTCTAATCTCTTACGCAAGACCTGCCTCAACCACTT

GATAAACTCTTTTGTCTACGTATTGAAAACAAAAGAGGCAAATAAACATC

TAGCCAAATGAAACACCAATAATGCTTTAAACAAAATGGAATAATTGCAT

CATCAATTAATCTTTATAAGTGAGAATTTTCCCTCCTATAATAATGCGCT

AGGTATCAATTTTCAACTCTGAAATATAAAGCTTCAAGCGTGTGTTATCA

AAAATCAAGCACAGTAAAATCATAAGCAGAATCATTGGTGATGCTAATAG

TTGATGTGGAATCGAACAATGTTCATATTCTGATACCTTGTTGGTGACAA

GTCAAGACCCTTATAGACTTGAATTTTGTCTGAGTTGATGATTTCAGAAG

GGGAATCTAGTATCTAAGTAGATGGTAAATTTATTTTTTCCAATTCCAGT

TGCTTCCATTATGAACAAACCTTATTCTTTTAGGCTAATATTGAGGAACA

AAAGCCACGGAATATTTTTTTATGTATAACCTAAGAAAAAGACAATAAT

AAAAATAATTAAAAACTACAACAGATGATTTTGGACTTGAATCGAATTGG

ATTAATCTTATACATGTTGTCGATAAGGATACTAGTTATATGAAGAAGAG

AATCAATTGAAACTTTATTTGTGCTATATATAATGATTTATGATATATGG

AGAGAGGGATGGCAGAATATGCAAGTTTGGAATCAATTCTGGACATTCAT

GGAGGGCGGGTTTATCATCGTGGGTGTGGTAGGGGTGGCTGAGGTTCTAG

GGCTACCCAGTACTTTTATGATGTTGTTGTAGTATTTTGAACAAATTTGT

TTTTTAATTTTATGTTTGAATATTGGGTTTGTAACATATGGATAATTTGT

TTTTAATTTTATGTTCGAAATTGTGTTGTTTTTGATCATTTTCATTACA

ATATTTATTTATTTATTCACGAATGCATGTTTATATCAACAAATTATATA

ATCTGTATGTATCATAGTGAAAACAAACTCTGTTTTTCTTTTGATACCTT

TCAGATTATATAATTTGAAATGTCATAAAACAGTTTAGATTATATAATCT

GAAATATGCGTTTTTTACACCACATTTTGCATTTTGTGAGGTGTTTGACA

CTTTTCGGATTATATAAGTCAAATTATTTTAAGAAGTTTCGGATTATATA

TCTGAAACATATGTTTAACTGACACATACACAAACATCTCTAGGGTGATT

TGTCTTCCAATAGTTTTTATACTGTTTGGATTATATAATCCGAATCAAGG

TTAAGAAAAATTAGGGCGCTCGAAAACCAAATAGGGTGGGAAAAGTAAT

GACCAATATTGATTACCCTATAAGGAGCCAAAGCCTGAAAAAAGTACCAT

ACATGATTGATATTTGTGGAGGCATTAATAGTCACAAAACTACACGTGGC

AATTTTATATTGGTGGCTAATGATAAGGCTAGCACAAAAATTTCCATTCC

TGTGTGGTTGATATGGCAGCAAAGTTTATCATATTCACAACCAACAAAAT

GGTATTATGAAGCATTACCACAATTTATAAGACCATAATATTGGAAATAG

GAAAATAAAAACATTATATATAGCAAGTTTGAGTATAAGCTTTGCAATTC

AAGCAGAAGTACATCTTACTTTACTAGTGAACTAAGTAAGGGAGAAAAAA

AATGGCTTCCTCTATGATGTCCTCTTCA

The gene constructs of the present invention may also include Rubisco Small Subunit Transit Peptide (RS), which increases the gene expression in chloroplasts. Rubisco Small Subunit Transit Peptide can increase the accumulation of protein in chloroplasts of transgenic plants. The majority of chloroplast proteins are encoded in the nucleus and synthesized in the cytosol as precursors with N-terminal extensions called transit peptides. The N-terminal transit peptide generally possesses necessary and sufficient information for the correct targeting of proteins to chloroplasts. Suyeon found that RS:Cel5A transgenic lines produced highly stable active enzymes, and the protein accumulation of these transgenic lines was up to 5.2% of the total soluble protein in the crude leaf extract, remaining stable throughout the life cycle of the tobacco plant. (See Suyeon Kim, Dae-Seok Lee, In Seong Choi, Sung-Ju Ahn, Yong-Hwan Kim, Hyeun-Jong Bae, *Arabidopsis thaliana* Rubisco small subunit transit peptide increases the accumulation of Thermotoga maritime endoglucanase Cel5A in chloroplasts of transgenic tobacco plants. Transgenic Res. 2010, (19):489-497, incorporated by reference herein in its entirety.)

The nucleic acid sequence of Rubisco Small Subunit Transit Peptide(RS) is:

[SEQ. ID. NO. 8]
ATGGCTTCCTCTATGCTCTCTTCCGCTACTATGGTTGCCTCTCCGGCTCA

GGCCACTATGGTCGCTCCTTTCAACGGACTTAAGTCCTCCGCTGCCTTCC

CAGCCACCCGCAAGGCTAACAACGACATTACTTCCATCACAAGCAACGGC

GGAAGAGTTAACTGCATGCAGGTGTGGCCTCCGATTGGAAAGAAGAAGTT

TGAGACTCTCTCTTACCTTCCTGACCTTACCGATTCCGAA

And the amino acid sequence is:

[SEQ. ID. NO. 9]
MASSMLSSATMVASPAQATMVAPFNGLKSSAAFPATRKANNDITSITSNG

GRVNCMQVWPPIGKKKFETLSYLPDLTDSE

The above regulatory sequences may be used in the gene constructs for insect/fungal resistance. They may be used to create such gene constructs (and the expression cassettes described above) using techniques that are known to those skilled in the art.

The plant to be transformed in various aspects of the present invention is preferably a plant susceptible to infestation and damage by insects and/or fungi. Such plants include *Arabidopsis* and Canola. However, this is not to be construed as limiting to these species, and these insects and fungi also infest certain other plants, for example, poplars and other woody plants. Thus the methods of this invention are readily applicable via conventional techniques to numerous plant species, if they are found to be susceptible to the plant pests described.

Further, while plants, and transformed or transgenic plants are discussed herein, the term "plant" may include the whole plant or any parts or derivatives thereof, such as plant cells, plant protoplasts, plant cell tissue cultures from which plants can be regenerated, plant calli, plant cell clumps, and plant cells that are intact in plants, or parts of plants, such as embryos, pollen, ovules, fruit, flowers, leaves, seeds, roots, root tips, and the like.

Further still, while various sequences of genes are described herein (such as sequences for LECRPA1, LECRPA2, and LECRPA3), it will be recognized by those skilled in the art that exact sequences need not be used in the transgenic plants (and other aspects of the present invention), so long as the sequence used is functional for its intended purpose (e.g., expression thereof provides resistance to an insect). Thus, aspects of the present invention contemplate variants of the genes and sequences described herein. As used herein, the term "variant" refers to nucleic acid sequences that are essentially similar to a given nucleic acid sequence. For example, the term "variants thereof" or refers to a polynucleotide sequence having one or more (e.g., two, three, four, five or more) nucleotides deleted (deletion variants) from said polynucleotide sequence or having one or more nucleotides substituted (substitution variants) with other nucleotides or one or more nucleotides inserted into said polynucleotide sequence (insertion variants). Sequences which are essentially similar to one another are nucleic acid sequences comprising at least about 90%, more preferably 91%, 92%, 93%, 94%, 95%, 96%, 97%, 98% or 99% or more nucleic acid sequence identity to one or more listed sequences.

In one illustrative embodiment, the DNA sequence, which when expressed imparts insecticidal and fungicidal activity, is a structural gene which codes for at least one of the selected plant lectins described herein. Alternatively, there may be used a construct of multiple genes coding for more than one of the lectins, such as for all three above-described lectins. Further, it will be recognized by those skilled in the art that other lectins may exhibit some insecticidal and/or fungicidal activity. Further, other proteins beside lectins may exhibit insecticidal and/or fungicidal activity. It would be within the purview of one skilled in the art to prepare gene constructs and transformed plants including such constructs based on the teachings herein.

Further, in general, since one aspect of the invention is to confer resistance to an insect or fungi to which the plant is susceptible, the selected lectin will not be native to the plant, i.e., the lectin will come from a species other than the plant being transformed. However, in species which produce insecticidal or fungicidal lectins but in lower than insecticidal or fungicidal amounts, it may be preferable to insert a gene for the native lectin under strong constitutive promoter control to cause overproduction of the lectin, thus achieving insecticidal and fungicidal levels and conferring effective insect and fungus resistance. Alternatively, where a plant produces a native larvicidal lectin but the lectin is not produced in or not distributed to tissues which are normally infested by the larvae, a tissue specific promoter can be used to provide localized expression or overproduction of the lectin. A tissue specific promoter can be used in any instance where it may be desirable to localize production of the lectin to an infested tissue or to a tissue which is efficient in production of the lectin.

In one embodiment of the present invention, transgenic *Arabidopsis* may be prepared with above-described genes using an *Agrobacterium* mediated plant transformation method. *Arabidopsis* is a relative of canola. *Arabidopsis* is thus an excellent model plant to test the effectiveness of creating insect-resistant and/or fungi-resistant plants. In another embodiment of the present invention, transgenic Canola may be prepared with above-described genes using techniques such as those described above, or other methods known to those skilled in the art (e.g., *Agrobacterium* mediated plant transformation, gene gun, or other physical or chemical methods for gene delivery).

Once transgenic plants are produced, a method of the present invention includes selecting those with high expression levels of the desired genes. Such transgenic plants with high expression levels of the desired genes may then be used for the desired resistance traits. Also, further experiments may be performed on such plants to determine the effectiveness of the resistance traits.

Further, a recent patent application and other research articles report the use of RPbAI to treat diseases of the gastrointestinal tract including mucositis (see PCT/GB98/02612). Since medical applications of RPbAI require large quantities of inexpensive, high quality RPbAI protein a transgenic plant source could be of commercial significance.

Thus, various aspects of the present invention contemplate: (A) molecular cloning and modifications of the three RPbAI/RPbAII genes, and construction of fusion genes for high expression in plants; (B) genetic transformation of plants (such as *Arabidopsis* or Canola); (C) characterization of expression levels of transgenes in the produced transgenic plants; (D) propagation of selected lines of transgenic plants; and (E) use of such plants for their resistance to insects and rot.

The following Examples further exemplify the gene constructs and transgenic plants of the various aspects of this invention and the methods of making and using them. However, it will be understood that other methods, known by those of ordinary skill in the art to be equivalent, can also be employed.

EXAMPLES

Example 1—*Agrobacterium* Mediated Transformation of Plants

In this Example, transgenic *Arabidopsis* is prepared with above-described genes using an *Agrobacterium* mediated plant transformation method. It will be noted that not all plants described in the various Examples below were transformed using this method, and other methods for transforming plants are well known, and have been described elsewhere in this application.

As is known to those skilled in the art, *Agrobacterium* is a genus of Gram-negative bacteria that uses horizontal gene transfer to cause tumors in plants. Transformation with *Agrobacterium* can be achieved in two ways. Protoplasts, or leaf-discs can be incubated with the *Agrobacterium* and whole plants regenerated using plant tissue culture. A common transformation protocol for *Arabidopsis* is the floral-dip method: the flowers are dipped in an *Agrobacterium* culture, and the bacterium transforms the germline cells that make the female gametes. The seeds can then be screened for antibiotic resistance (or another marker of interest), and plants that have not integrated the plasmid DNA will die.

*Agrobacterium tumefaciens* is the most commonly studied species in this genus and infects the plant through its Ti plasmid. The Ti plasmid integrates a segment of its DNA, known as T-DNA, into the chromosomal DNA of its host plant cells. The plasmid T-DNA that is transferred to the plant is an ideal vehicle for genetic engineering. This is done by cloning a desired gene sequence into the T-DNA that will be inserted into the host DNA (and so gene constructs for LECRPA1, 2, and 3 may be inserted in this fashion). *Arabidopsis* may be transformed by dipping their flowers into a broth of *Agrobacterium*: the seed produced will be transgenic.

Floral Dip Transformation of *Arabidopsis*

Plants were typically planted 6-20 per 64 cm$^2$ pot in moistened potting soil. To obtain more floral buds per plant, inflorescences were clipped after most plants had formed primary bolts, relieving apical dominance and encouraging synchronized emergence of multiple secondary bolts. Plants were dipped when most secondary inflorescences were about 1-10 cm tall.

Inoculation of Plants

*Agrobacterium tumefaciens* cultures were typically started from a 1:100 dilution of smaller overnight cultures and grown for roughly 18-24 h. Cells were harvested by centrifugation for 20 min at room temperature at 5500 g and then re-suspended in infiltration medium to a final OD600 of approximately 0.80 prior to use. The revised floral dip inoculation medium contained 5.0% sucrose and 0.05% Silwet L-77. For floral dip, the inoculum was added to a beaker, plants were inverted into this suspension such that all above ground tissues were submerged, and plants were then removed after 3-5 sec of gentle agitation. Plants were left in a low light or dark location overnight and returned to the greenhouse the next day. Plants were grown for a further 3-5 weeks until siliques were brown and dry.

Selection of Putative Transformants

Seeds were surface sterilized by liquid sterilization, seeds were first treated with 95% ethanol for 30-60 sec, then with 50% bleach containing 0.05% Tween 20 for 5 min, followed by three rinses with sterile water. To select for transformed plants, sterilized seeds were suspended in 0.1% sterile agarose and plated on kanamycin selection plates at a density of approximately 3000 seeds per 150*15 mm2 plate, cold-treated for 2 days, and then grown for 7-10 days in a controlled environment at 24° C. Selection plates contained ½×MS medium, 0.8% agar, 50 mg ml-1 kanamycin mono sulfate. Petri plates and lids were sealed with surgical tape for the first week of growth. Excess moisture during growth was removed by briefly opening the plates and shaking moisture off the lid. Transformants were identified as kanamycin resistant seedlings that produced green leaves and well established roots within the selective medium. (See Clough, S. J. and Bent, A. F. (1998) Floral dip: a simplified method for *Agrobacterium*-mediated transformation of *Arabidopsis thaliana*. Plant J. 16, 735-743, and Labra, M., Vannini, C., Grassi, F., et al. (2004) Genomic stability in *Arabidopsis thaliana* transgenic plants obtained by floral dip. Theor. Appl. Genet. 109, 1512-1518.)

Example 2—Transformation Oilseeds (*B. napus* CV Westar) Mediated by *Agrobacterium tumefaciens*

Seeds from *B. napus* CV Westar were surface-sterilized in a 50% bleach solution for 15 min with vigorous shaking. The seeds were then germinated on MS basal. After 7 days, the seedlings were collected and the hypocotyls were cut into 1-2 cm pieces. The hypocotyl sections were placed on MS basal medium with 1 mg/L of 2,4-D for 24 h to precondition the material. Hypocotyls were inoculated with an *Agrobacterium* for 30 min and co-cultivated on solid MS basal medium with 1 mg/L of 2,4-D for 3 days. Plant tissue was moved to the same media containing 150 mg/L of timintin to kill the *Agrobacterium*, and 25 mg/L of kanamycin to select for transformed cells. After 7 days, the hypocotyls were transferred to basal medium containing 4 mg/L of 6-BAP, 0.4 mg/L of NAA, 0.5 mg/L of GA3, 5 mg/L of silver nitrate, and the above antibiotics, for organogenesis. (See Cardoza, V. and C. N. Stewart. Increased *Agrobacterium*-mediated transformation and rooting efficiencies in canola (*Brassica napus* L.) from hypocotyl segment explants. Plant Cell Rep. 2003. 21:599-604, and Priti Maheshwari, Gopalan Selvaraj, Igor Kovalchuk. Optimization of *Brassica napus* (canola) explant regeneration for genetic transformation, New Biotechnology, 2011, 29(1) 144-156.)

Example 3—Transformation of Poplar

Poplar (*Populus tomentosa*) was also transformed, using the methods described in Cseke L J, Cseke S B, Podila G K. *High efficiency poplar transformation*. Plant Cell Rep, 2007, 26(9):1529-38, incorporated by reference herein in its entirety.

Materials

Materials used in the transformation included (1) young sterile poplar (*Populus tomentosa*) plants; and (2) *Agrobacterium* strains EHA105; plasmid: pCAMBIA0386-RPA123 and pCAMBIA0386-atNRT2.1.

Explants Preparation

Healthy fully expanded leaves were taken from tissue culture grown poplar plant. The leaves were then cut into 0.3-0.5 cm squares. The leaf disks were transferred into a sterile 50-ml corning tube, which contained about 2 ml liquid Co-cultivation medium (2.41 g/L WPM+30 g/L Sugar+20 mg/L Acetosyringone).

Bacterial Suspension

*Agrobacterium* cells were collected from liquid culture using a centrifuge at 2,500×g for 1 min. The liquid was discarded, and the bacterial pellet was suspended using the liquid Co-cultivation medium. The suspension was then diluted to an O.D.600 of 0.5-0.8.

Infection

The bacterium suspension was transferred to a corning tube with the explants. The leaf explants were incubated with bacterium at 28° C. with a gentle shaking at 100 rpm for 20 min. The bacterium suspension was then poured off. And the explants were transferred, 15-20/petri-dish, to the plates with Co-cultivation solid medium (2.41 g/L WPM+30 g/L Sugar+7 g/L Agarose+20 mg/L Acetosyringone).

Co-Cultivation

Co-cultivation was carried out at 25° C. in the dark for 3 days.

Callus Induction

The explants were transferred, 12 pieces/dish, to the callus inducing medium (2.41 g/L WPM+30 g/L Sugar+7 g/L Agarose+2 mg/L 6-BA+1 mg/L NAA+30 mg/L Kanamycin+150 mg/L Timentin). The explants were then cultured at 25° C. in the dark for 3-4 weeks.

Shoot Induction

The explants were transferred, 10 pieces/dish, to the shoot-inducing medium (2.41 g/L WPM+30 g/L Sugar+7 g/L Agarose+1 mg/L 6-BA+0.1 mg/L NAA+40 mg/L Kanamycin+Timentin 150 mg/L). The explants were then cultured at 25° C. at 16-hours photoperiod for 3-4 weeks until shoots were produced.

Root Induction 2 cm or taller shoots were cut from the explants and transferred to a root formation medium (2.41 g/L WPM+30 g/L Sugar+7 g/L Agarose+50 mg/L Kanamycin+150 mg/L Timentin). These shoots were cultured at a 16-hour photoperiod for 3-4 weeks until roots were produced and the plants reached to 12 cm in height.

Acclimation and Transplantation

Well-rooted plantlets were removed from culture medium, agarose was washed off with tap water and the plantlets were kept in the box with roots in water for 3 days. The acclimatized plants were subsequently grown in larger pots filled with soil.

Example 4—Susceptibility of Transgenic Plants to Fungi/Rot

In the two experiments of this Example, transgenic canola plants (and portions thereof) were exposed to microorganisms, to compare the adverse effects of the microorganisms on leaves from the transgenic plants to the effects on leaves of wild type plants. The canola plants were transformed by known methods, as disclosed by Priti Maheshwari, Gopalan Selvaraj, Igor Kovalchuk. *Optimizations of Brassica napus* (*canola*) *explant regeneration for genetic transformation*. New Biotechnology, 2011, 29(1)144-155, incorporated by reference herein in its entirety; and Cardoza, V. and C. N. Stewart. *Increased Agrobacterium-mediated transformation and rooting efficiencies in canola* (*Brassica napus* L.) *from hypocotyl segment explants*. Plant Cell Rep, 2003. 21:599-604, incorporated by reference herein in its entirety.

The studies described in Experiments 1 and 2 (below) used transgenic canola plants including a LECRPA1+2+3 construct. Canola plants were transformed by methods such as those described herein. Polymerase chain reaction (PCR) was used to confirm the insertion of the transgenes into canola plants, and real time PCR was used to determine the expression levels of the transgenes in canola.

Figure 2:
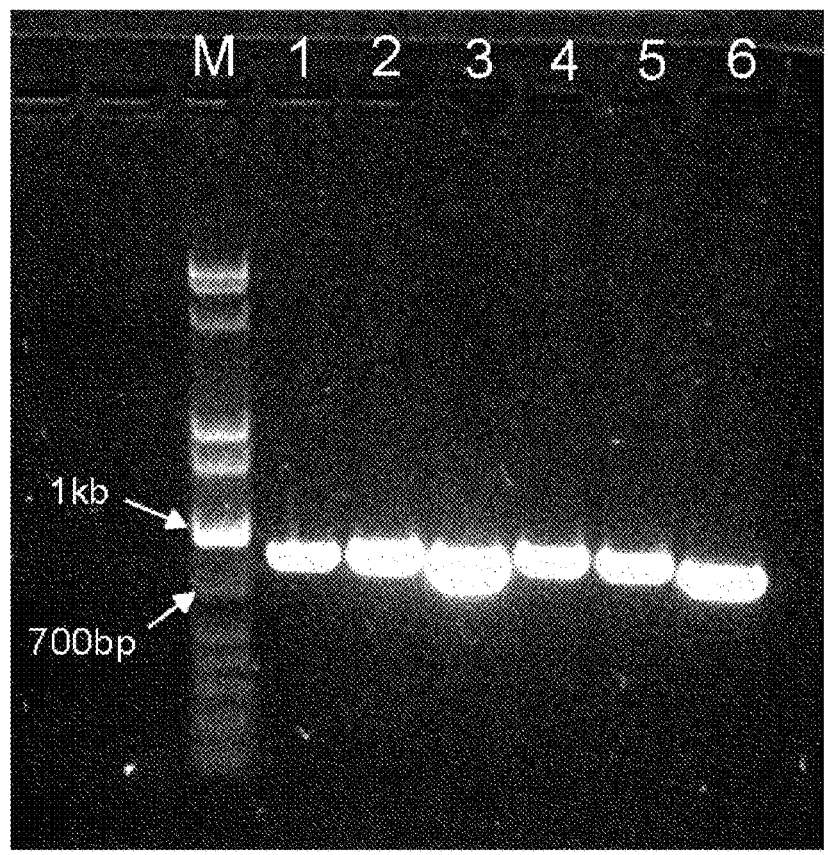
FIG. 2 is a photograph verifying the transformation of a plant to include the LECRPA1, LECRPA2, and LECRPA3 genes.

As described above, the confirmation of insertion of the transgenes into canola plants is shown in FIG. 2. To that end, the methods described by Ahmed et al (2009) for canola genomic DNA isolation [Ahmed, I., M. Islam, W. Arshad, A. Mannan, W. Ahmad, B. Mirza (2009): *High-quality plant DNA extraction for PCR: an easy approach*. Journal of Applied Genetics. 50: 105-107, incorporated by reference herein in its entirety] and the method by Chen et al (2006) for PCR reactions [Chen Y., L. Lu, W. Deng, X. Yang, R. McAvoy, D. Zhao, Y. Pei, K. Luo, H. Duan, W. Smith, C. Thammina, X. Zheng, D. Ellis, Y. Li (2006): *In vitro regeneration and Agrobacterium-mediated genetic transformation of Euonymus alatus* Plant Cell Reports. 25(10):1043-51, incorporated by reference herein in its entirety] were used. Basically, to isolate genomic DNA from the canola plant, 2 grams of leaf tissues were used in extracting genomic DNA therefrom using an extraction buffer (100 mM Tris-HCl, 100 mM EDTA, 250 mMNaCl) and 1.5-mL microfuge tubes, followed by cell lysis with 20% SDS, and DNA extraction with phenol: chloroform: iso-amyl alcohol (25:24:1). Hydrated ether was then used to remove polysaccharides and other contaminants from the DNA preparation. Taq DNA polymerase and three sets of primer sequences were then used to amplify the three genes (LECRPA1, LECRPA2, and LECRPA3) independently via PCR.

The primer sequences used in this Example were as follows:

```
pRPA1-F:
                                     [SEQ. ID. NO. 10]
ATGACTTCCTACAACTTC, pRPA1-R:
                                     [SEQ. ID. NO. 11]
TCATGCAGCATAGGTTGA,
(product size 858 bp);

pRPA2-F:
                                     [SEQ. ID. NO. 12]
ATGGCTTCCTACAAGTTC,
```

-continued pRPA2-R:
TCATGCAGCATAGGTTGA, [SEQ. ID. NO 13]
(product size 861 bp); and pRPA3-F:
ATGCTCATAAGTTTCTTTG, [SEQ. ID. NO. 14]

pRPA3-R:
TCATGCATAGCTTGCAAT, [SEQ. ID. NO. 15]
(product size 783 bp).

For the PCR conditions, a reaction mix was prepared in accordance with the following Table 1:

| Reagent | Volume | Final Conc. |
| --- | --- | --- |
| 2 X CloneAmpHiFi PCR Premix | 10 μl | 1X |
| Primer 1 (10 μM) | 0.5 μl | 0.25 μM |
| Primer 2 (10 μM) | 0.5 μl | 0.25 μM |
| DNA Template | 0.5 μl | (<100 ng) |
| Sterilized distilled water | 8.5 μl | |
| Total volume per reaction | 20.0 μl | |

The reaction mixture(s) was then placed in a thermocycler under the following parameters: (1) 98° C. for 3 minutes; (2) 34 cycles of 98° C. for 10 seconds, 68° C. for 15 seconds, and 72° C. for 1 minute; (3) 72° C. for 5 minutes; and (4) a hold at 12° C. (the hold may last indefinitely). PCR products were then analyzed with gel electrophoresed with the Ti plasmid DNA eliminated from the template before PCR reactions were conducted [Chen et al (2006)] (products were run on an agarose gel to check the result and DNA fragments were extracted from the agarose gel). The presence of the three transgenes indicates that the canola plants produced were transgenic—these results are shown in FIG. 2.

The insertion of the transgenes into the genome of the canola plants was further verified by real time PCR—and particularly used to determine the expression levels of the inserted genes in the canola plants. To that end, total RNA of transgenic canola plants was prepared using the RNeasy Plant Mini Kit (commercially available from Qiagen, Valencia, Calif.) according to the manufacturer's instructions. RNase-free DNase set (Qiagen) was used to eliminate genomic DNA contamination of all the RNA samples. The following protocol was used:

1) Determine the amount of plant material. Do not use more than 100 mg.
2) Immediately place the weighed tissue in liquid nitrogen, and grind thoroughly with a mortar and pestle. Decant tissue powder and liquid nitrogen into an RNase-free, liquid-nitrogen-cooled, 2 ml microcentrifuge tube. Allow the liquid nitrogen to evaporate, but do not allow the tissue to thaw. Proceed immediately to step 3.
3) Add 450 μl Buffer RLT to a maximum of 100 mg tissue powder. Vortex vigorously. Short 1-3 min incubation at 56° C. may help to disrupt the tissue.
4) Transfer the lysate to a QIAshredder spin column (lilac) placed in a 2 ml collection tube, and centrifuge for 2 min at full speed. Carefully transfer the supernatant of the flow-through to a new microcentrifuge tube without disturbing the cell-debris pellet in the collection tube. Use only this supernatant in subsequent steps.
5) Add 0.5 volume of ethanol (100%) to the cleared lysate, and mix immediately by pipetting. Do not centrifuge. Proceed immediately to step 6.
6) Transfer the sample, including any precipitate that may have formed, to an RNeasy spin column (pink) placed in a 2 ml collection tube (supplied).Close the lid gently, and centrifuge for 15 s at 8000×g (10,000 rpm). Discard the flow-through.
7) Add 700 μl Buffer RW1 to the RNeasy spin column. Close the lid gently, and centrifuge for 15 s at 8000×g (10,000 rpm) to wash the spin column membrane. Discard the flow-through.
8) Add 500 μl Buffer RPE to the RNeasy spin column. Close the lid gently, and centrifuge for 15 s at 8000×g (10,000 rpm) to wash the spin column membrane. Discard the flow-through.
9) Add 500 μl Buffer RPE to the RNeasy spin column. Close the lid gently, and centrifuge for 2 min at 8000×g (10,000 rpm) to wash the spin column membrane.
10) Optional: Place the RNeasy spin column in a new 2 ml collection tube (supplied),and discard the old collection tube with the flow-through. Close the lid gently, and centrifuge at full speed for 1 min.
11) Place the RNeasy spin column in a new 1.5 ml collection tube (supplied). Add 30-50 μlRNase-free water directly to the spin column membrane. Close the lid gently, and centrifuge for 1 min at 8000×g (10,000 rpm) to elute the RNA.

Total RNA was isolated from the leaves using the QIAGEN RNA isolation kit. And then 1 ug RNA was used to synthesize cDNAs with a cDNA synthesis kit (known to those skilled in the art). One tenth of the volume of the first-strand cDNA reaction was used for RT-PCRs to amplify the LECRPA3 gene (using the primers—RPA3-F: CACCAACTTCACCAGAGGTG [SEQ. ID. NO. 16], RPA3-R: CACGGCCTGTATTCCAAGTAGG [SEQ. ID. NO. 17]).

UBC9 (ubiquitin-conjugating enzyme 9) was used as a reference gene (see Chen X, Truksa M, Shah S, Weselake R J. *A survey of quantitative real-time polymerase chain reaction internal reference genes for expression studies in Brassica napus*. Anal Biochem. 2010, 405(1):138-40, incorporated by reference herein in its entirety). Primers used for the reference gene were UBC9-F:GCATCTGCCTCGACATCTTGA [SEQ. ID. NO. 18], UBC9-R:GACAGCAGCACCTTGGAAATG [SEQ. ID. NO. 19].

For real time PCR, each 20 microliter (ul) reaction mixture was as follows for production of cDNA:

| Material | Volume |
| --- | --- |
| 5X cDNA systhesis buffer | 4 ul |
| dNTP Mix | 2 ul |
| RNA primer | 1 ul |
| RT enhancer | 1 ul |
| Verso enzyme mix | 1 ul |
| Template (RNA) | 1-5 ul |
| Water, nuclease-free (#R0581) | To 20 ul |
| Total Volume | 20 ul | cDNA synthesis was then run at 42° C. for 30 min (for 1 cycle), and inactivation was achieved at 95° C. for 2 minutes (for 1 cycle).

20 ul reaction of real time PCR was as follows: (1) 2× EvaGreen SUPERMIX—10 ul, (2) Sterile Water—7 ul, (3) 10 uM primer 1—1 ul, (4) 10 uM primer 2—1 ul.

Final primer concentration=500 nm each. Add 1 ul template/20 ul reaction (1-10 ng cDNA)

The protocol used in the real time PCR was as follows: Real-Time PCR was performed in an optical 96-well plate with BIORAD CFX96 real time PCR machine and universal cycling conditions (98° C. for 3 min, 40 cycles of 5s at 98° C. and 60° C. for 5 s) in final volume of 20 ml.

A no template control (NTC) was also included in each run for each gene. Experiment was conducted in three technical replicates. The normalized expression of RPA3 gene was automatically determined for each reaction using the BioRAD CFX96 manager 2.0 software.

Figure 3:
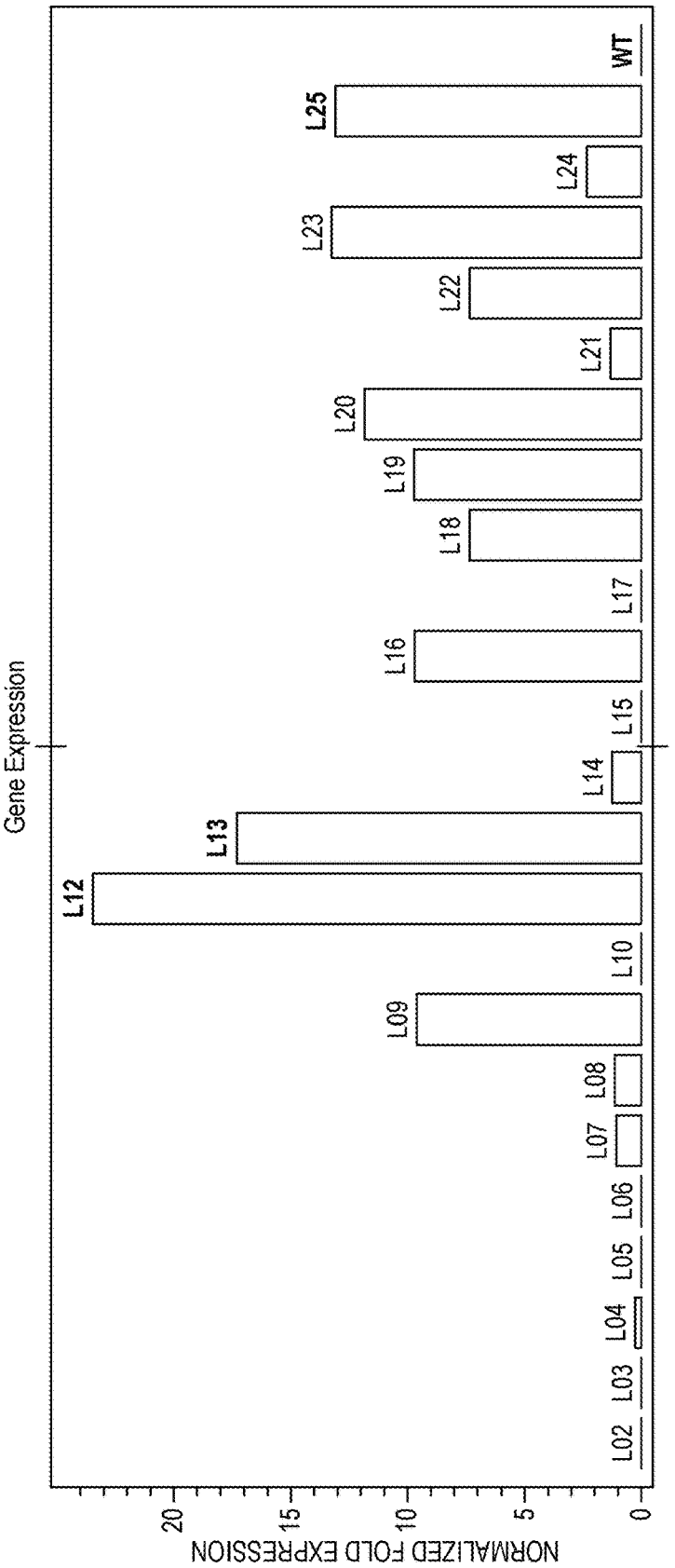
FIG. 3 is a graph showing the verification of expression of the LECRPA3 gene in transgenic plants including the LECRPA1+2+3 construct, using real time PCR.

As can be seen from FIG. 3, expression was pronounced in Lines 12, 13, and 25. These lines were used in subsequent experiments (as described in greater detail below).

Experiment 1

In the first experiment (conducted from Dec. 2, 2013 through Dec. 12, 2013), transgenic canola lines were identified and used. In particular, lines 12, 13, and 25 (as shown above in FIG. 3) were used, along with a wild type control. The leaves from each of lines 12, 13, and 25, and the wild type control were exposed to microorganisms, and the leaves were then allowed to sit in an environment conducive to fungus/rot. The leaves were observed to see how they were affected over time.

More specifically, in this experiment, used Pro-Mix soil was used as a source of microorganisms (a mixture of un-identified fungi and bacteria). Leaves of the same age from the wild-type control and from transgenic plants of lines 12, 13, and 25 were detached from plants, and then were buried in wet, used Pro-Mix soil.

Figure 13:
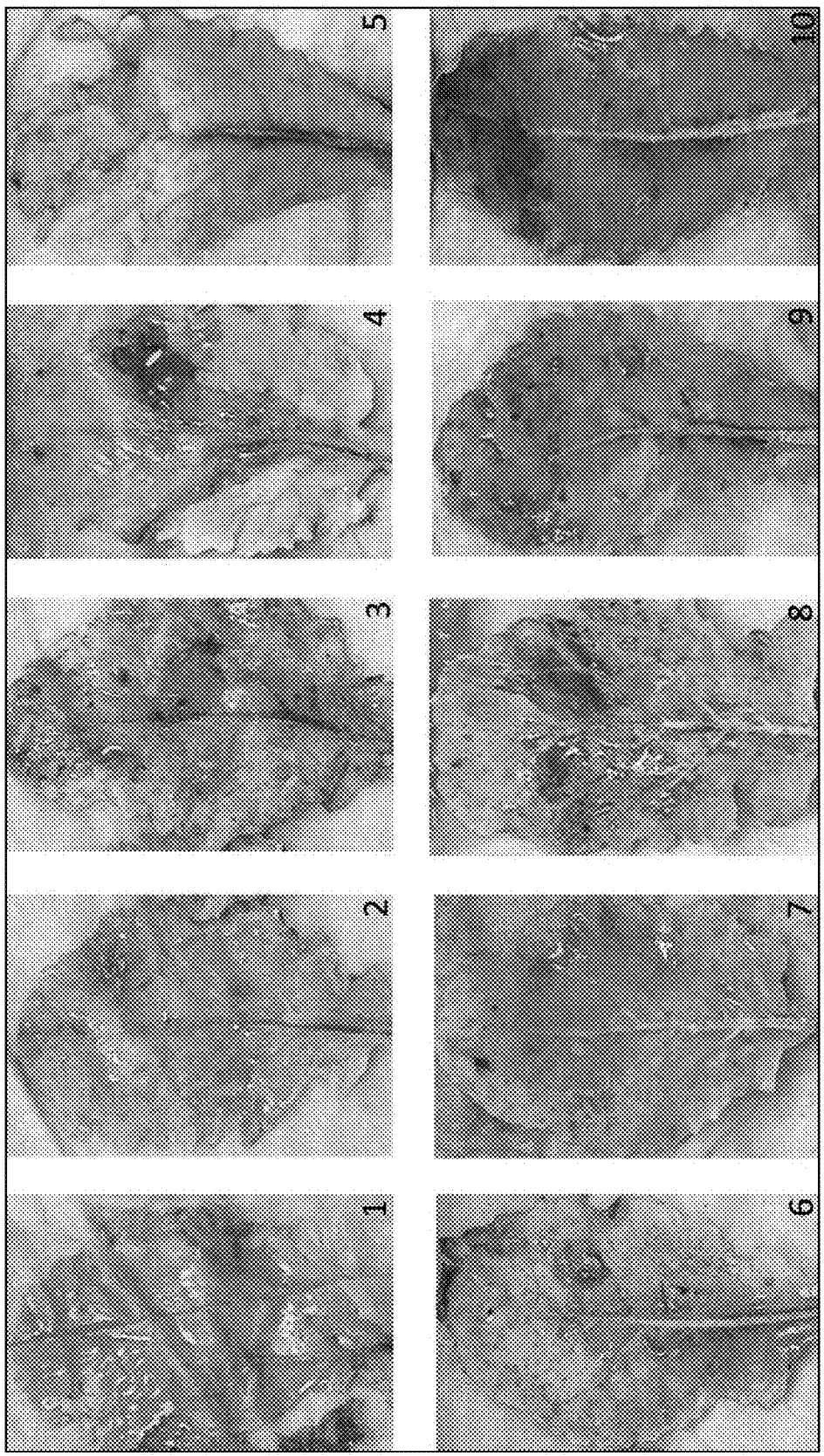
FIG. 13 is a photograph showing a scoring system used in scoring rotting in leaves in examples of the present application.

At days 10 and 14, the leaves were observed, and leaf rotting was scored, with photos taken of representative leaves. The scoring system used to estimate severity of rotting was 1 to 10, with "1" as the most severely rotted tissues, and "10" as the least rotted tissues. FIG. 13 is a photograph showing representative states of leaves that would be scored 1, 2, 3, 4, 5, 6, 7, 8, 9, or 10. These were used as comparative standards for scoring the leaves tested in this experiment.

Figure 4:
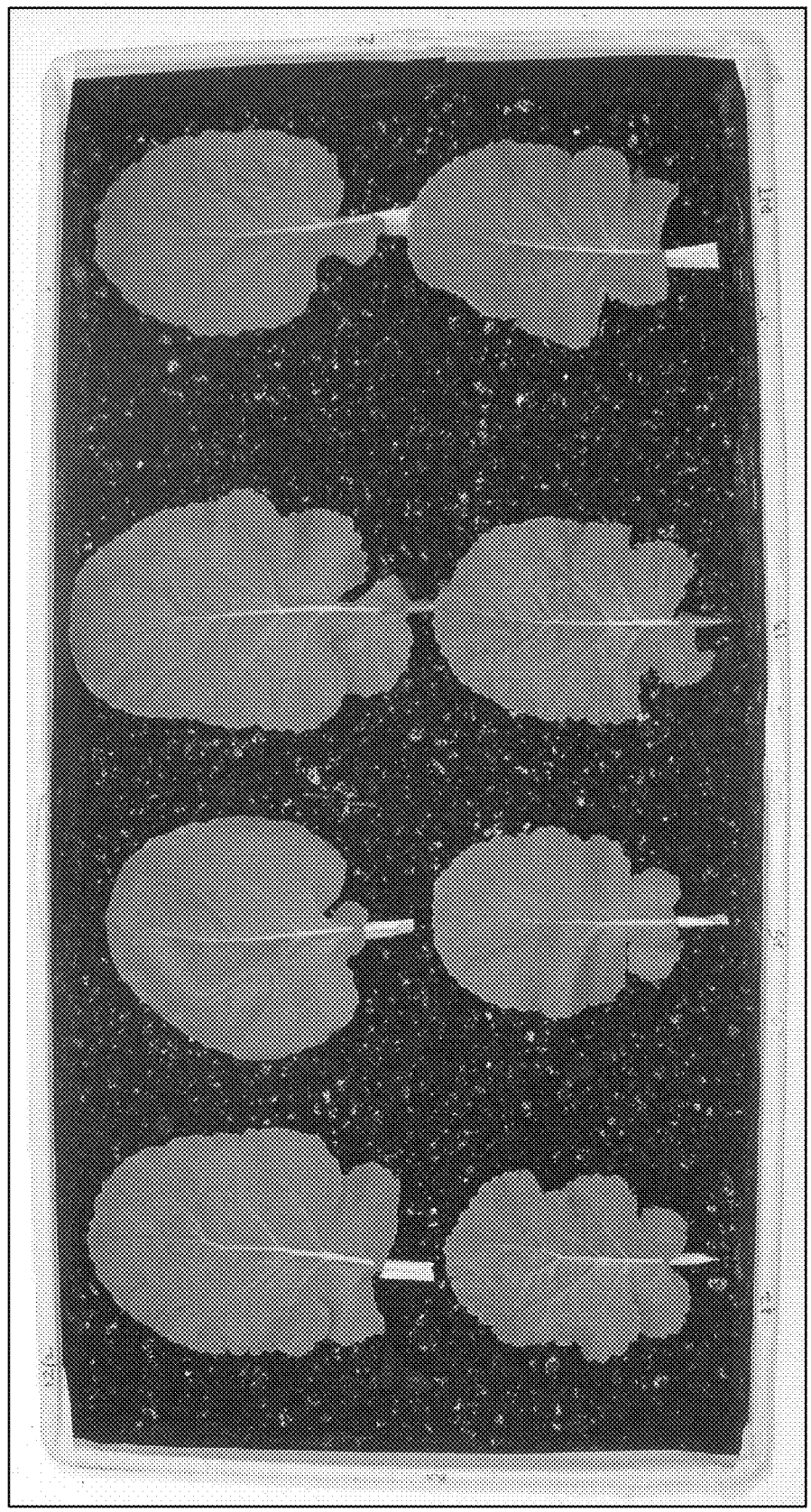
FIG. 4 is a photograph showing detached leaves from three transgenic plant lines and wild type leaves at Day 0 and prior to being buried in soil.
Figure 5:
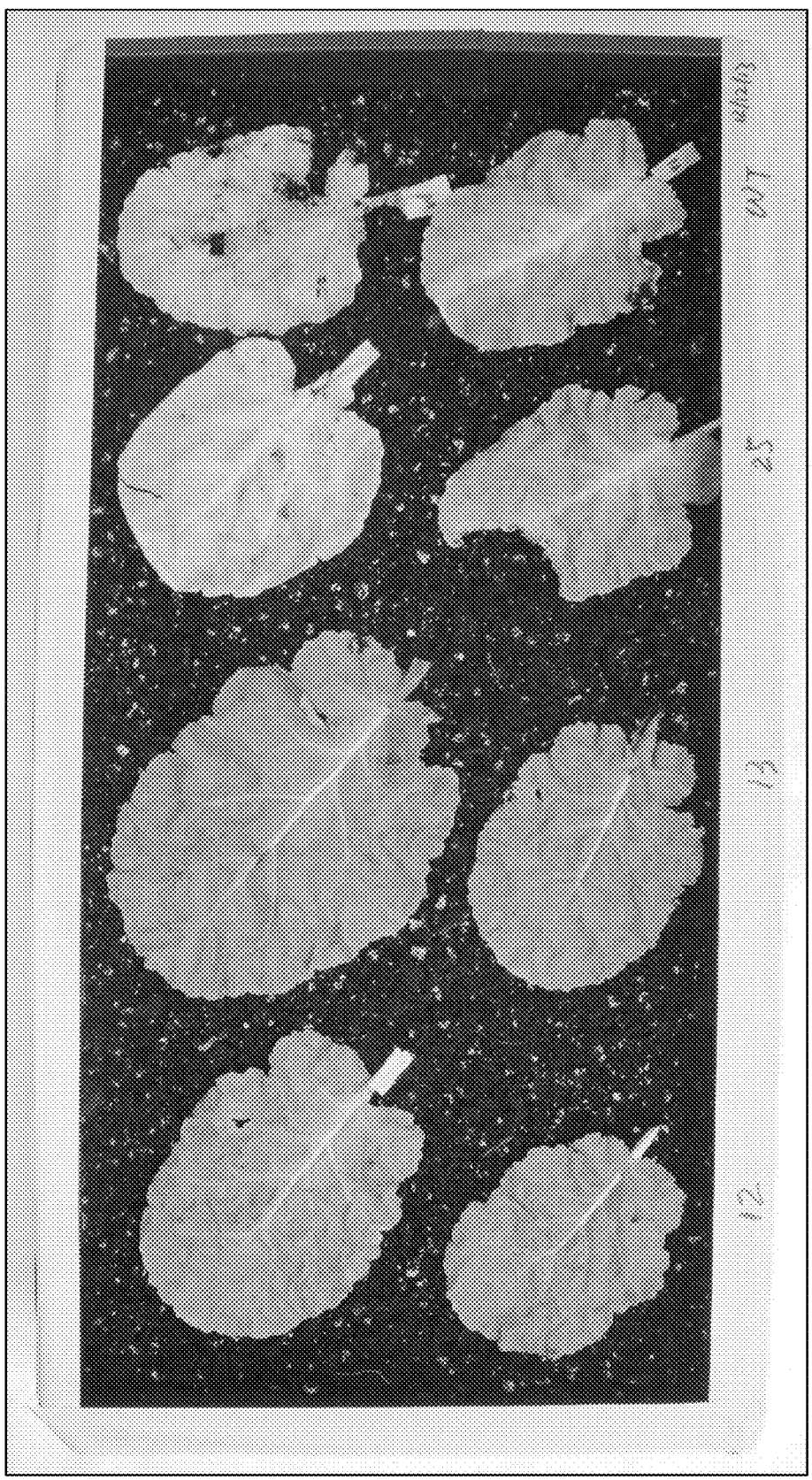
FIG. 5 is a photograph of the leaves in FIG. 4 after 10 days.
Figure 6:
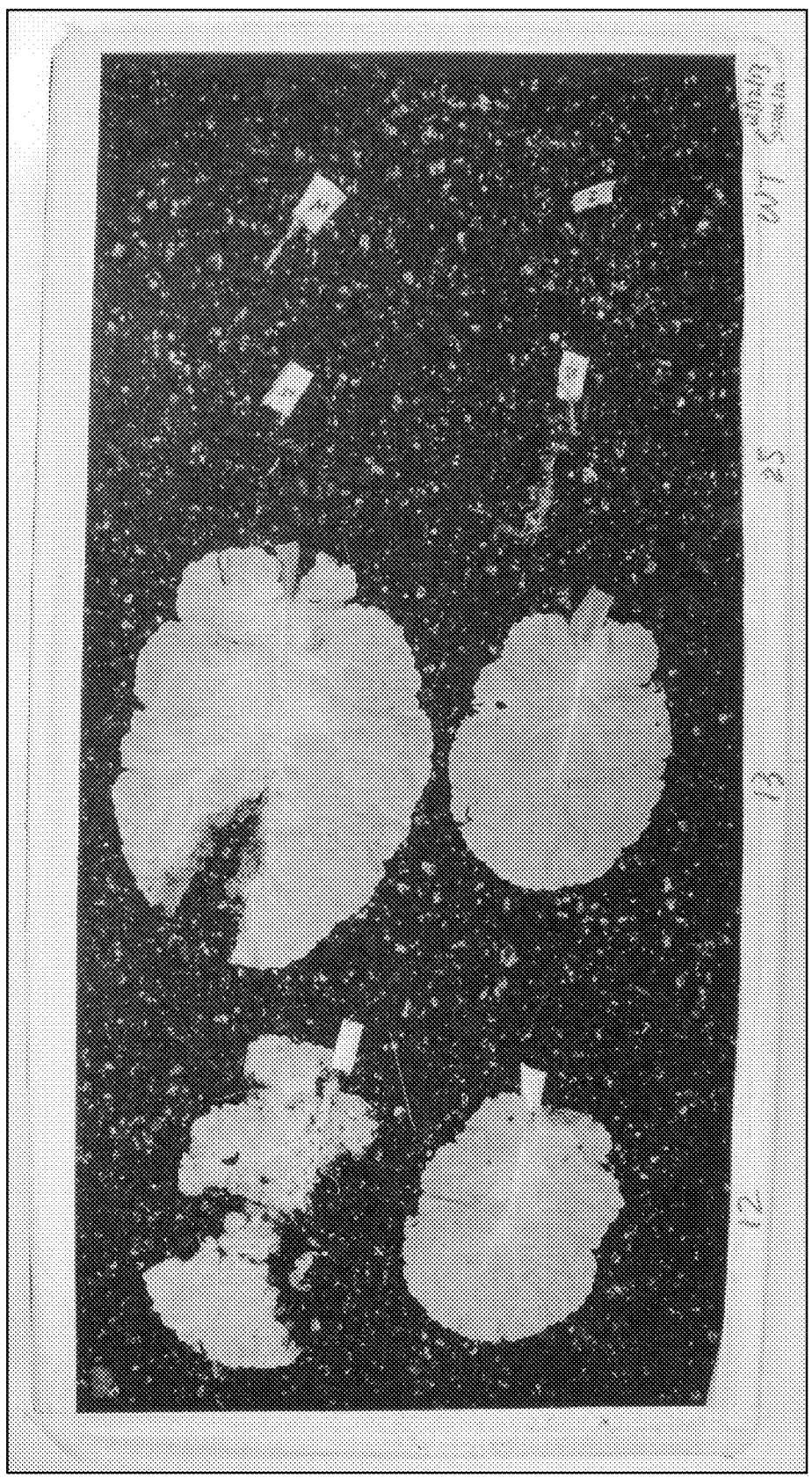
FIG. 6 is a photograph of the leaves of FIG. 4 after 14 days.

FIGS. 4-6 show the photographs of the leaves after an inoculation with mixture of microorganisms from used Pro-Mix soil at 0 days, 10 days, and 14 days, respectively.

Referring to FIG. 4, leaves are shown at day 0. Detached leaves of the same age (both wild type control, and transgenic leaves) are shown as photographed right before being buried in contaminated wet soil. In the Figure, "WT"=leaves from wild type plants (the leaves at the far right side of the photograph), and "12," "25," and "13"=leaves from transgenic plant lines 12, 25, and 13 (in that order being the three sets of leaves beginning at the left side of the photograph). As can be seen, at Day 0, no leaves exhibit any signs of rotting.

Referring to FIG. 5, leaves are shown 10 days after being buried in the contaminated, wet soil. The soil on the surfaces of the leaves was gently removed before the photo was taken. Leaves from transgenic lines 12 and 13 appear to be more resistant to rot. While line 25 shows some rot, none of lines 12, 13, or 25 show as much rot as the wild type leaves. (And, as seen above with respect to FIG. 3, lines 12 and 13 have higher expression levels of the transgenes, based on the PCR data.)

Referring to FIG. 6, leaves are shown 14 days after being buried in contaminated, wet soil. The soil on leaf surfaces was gently removed before the photo was taken. Again, the leaves from transgenic lines 12 and 13 appear to be more resistant to rot. As shown in FIG. 6, leaves from transgenic lines 12 and 13 can be seen, while leaves from line 25 and wild type plants have been destroyed completely by fungi and bacteria. (As described above with respect to FIG. 3, lines 12 and 13 have higher expression levels of the transgenes based on the PCR data.)

Experiment 2

In the second experiment (conducted from Feb. 21, 2014 through Mar. 2, 2014), a transgenic canola line was identified and used. In particular, line 13 (as shown above in FIG. 3) was used, along with a wild type control. The leaves from line 13 and the wild type control were exposed to microorganisms, and the leaves were then allowed to sit in an environment conducive to fungus/rot. The leaves were observed to see how they were affected over time.

In Experiment 2, three sources of microorganisms were used. Source One was used Pro-Mix soil (obtained from a lab at the University of Connecticut). The used Pro-Mix soil was mixed with distilled water (approximately a 1:3 ratio, volume) to extract microorganisms. Ten minutes later, the liquids were collected, and particles in the liquids were removed by filtration.

Source Two was rotted/rotting wood tissues collected from outdoors (at the University of Connecticut). The rotting/rotted wood tissues were soaked in distilled water (approximately a 1:3 ratio, volume) to extract microorganisms. Ten minutes later, clear liquids were collected.

Source Three was field soil collected at the University of Connecticut. The field soil was mixed with distilled water (approximately a 1:3 ratio, volume) to extract microorganisms. Ten minutes later, the liquids were collected, and particles in the liquids were removed by filtration.

Leaves and stems from the wild type controls and transgenic plants (of line 13) were inoculated for 5 minutes by immersing them in the liquids from each of the three sources (described above) that contained the mixture of microorganisms. The leaves and stems were then placed on wet paper towels in trays and the trays were covered with food wrap film to reduce water loss.

The trays were then left on a lab bench for 9 days. At day 10, photos were taken, and rotting of leaves and stems were scored. The scoring system used to estimate severity of rotting was a scale of 1 to 10, with "1" as the most severely rotted tissues, and "10" as the least rotted tissues. As with Experiment 1, FIG. 13 is a photograph showing representative states of leaves that would be scored 1, 2, 3, 4, 5, 6, 7, 8, 9, or 10. These were used as comparative standards for scoring the leaves tested in this Experiment 2.

Table 2 (below) summarizes the rotting scores of all treatments.

TABLE 2

| Rotting Scores | | | |
| --- | --- | --- | --- |
| Plant Line | Organ Tested | Microorganisms | Mean Score +/− SD |
| WT | Leaf | Used Pro-Mix | 3.83 +/− 3.82 |
| #13 | Leaf | Field Soil | 9.17 +/− 0.75 |
| WT | Leaf | Rotted Wood | 1.50 +/− 1.27 |
| #13 | Leaf | Used Pro-Mix | 5.56 +/− 3.58 |
| WT | Leaf | Field Soil | 1.86 +/− 1.46 |
| #13 | Leaf | Rotted Wood | 4.00 +/− 3.70 |
| WT | Stem | Used Pro-Mix | 6.92 +/− 1.88 |
| #13 | Stem | Field Soil | 6.08 +/− 1.73 |
| WT | Stem | Rotted Wood | 5.25 +/− 1.71 |
| #13 | Stem | Used Pro-Mix | 6.17 +/− 2.08 |

TABLE 2-continued

Rotting Scores

| Plant Line | Organ Tested | Microorganisms | Mean Score +/− SD |
|---|---|---|---|
| WT | Stem | Field Soil | 4.92 +/− 1.50 |
| #13 | Stem | Rotted Wood | 7.08 +/− 1.16 |

Note:
Means +/− SD (Standard Deviation).
WT: Wild-type canola.
13: Transgenic line 13.
The scoring system used: 1 to 10 used to estimate severity of rotting with "1" as the most severely rotted tissues, and "10" as the least rotted tissues (see FIG. 13).

Figure 7:
FIG. 7 is a photograph showing detached leaves from one transgenic plant line and wild type leaves at Day 10 after being inoculated with microorganisms from a first soil source.
Figure 8:
FIG. 8 is a photograph showing detached leaves from one transgenic plant line and wild type leaves at Day 10 after being inoculated with microorganisms from a second soil source.
Figure 9:
FIG. 9 is a photograph showing detached leaves from one transgenic plant lines and wild type leaves at Day 10 after being inoculated with microorganisms from a rotting wood source.

As can be seen from the table above, leaves and stems from wild type control plants exhibited more rotting than those from line 13 (with a more pronounced difference in the leaves). FIGS. 7-9 show the condition of the leaves (wild type and line 13) for each of the three sources (after 10 days). FIG. 7 shows the leaves inoculated with microorganisms from used Pro-Mix soil. FIG. 8 shows the leaves inoculated with microorganisms from field soil. And FIG. 9 shows the leaves inoculated with microorganisms from rotted/rotting wood.

Observations and Conclusions of Experiments 1 and 2:

Leaves from transgenic lines 12 and 13, particularly Line 13 appeared to be more rot resistance (resistant to mixture of unidentified bacteria and fungi).

Example 5—Susceptibility of Transgenic Plants to Termites

As one of the most destructive insect pests in the world, termites' damage to infrastructure, agricultural commodities and forestry resources exceeds $30 billion per year. The cryptic nature and tenacious foraging behavior of termites pose a real challenge to research and control efforts. For years, termite treatments have primarily relied on synthetic chemicals which are persistent (>5 years) and highly toxic, posing a serious threat to ecosystems and non-target organisms. The genetic-based strategy of the present application offers low impact on non-target organisms, which, in the long run, could lead to sustainable management of termites. This Example examines the susceptibility of testing plant materials to termite infestation.

2. Materials and Methods 2.1 Termites

The Eastern subterranean termite, *Reticulitermes flavipes*, is one of the most common termite species in the world. Three *R. flavipes* colonies, R13-2013, R18-2013 and R19-2013, were collected in 2013 from Daniel Boone National Forest (Wildcat Trail #228, KY, 37° 47' N 83° 35' W, Lexington, Ky., USA). These colonies have been maintained in complete darkness at 27±1° C. and 80±1% relative humidity, and were provisioned with hard wood mulch for more than six months before the experiment.

2.2 Testing Materials

Testing materials included: (1) transgenic lines of canola plants and (2) various types of woody materials. The transgenic lines of canola included tissues from two transgenic lines of canola (lines 12 and 13—shown in FIG. 3 as exhibiting high levels of transgene expression). These tissues, including leaves and stems, were provided to termites as the only food source. Control groups were fed with leaves and stems of a wild-type canola.

The various types of woody materials included willow, black locust, burning bush, and poplar. These were separately provided to other termites as the only food source with cellulose paper as control.

And finally, woody materials with or without bark, including poplar with or without bark were used for the testing with cellulose paper as control. A list of the various materials used appears in Table 3, below:

TABLE 3

List of Testing Materials

| Label* | Plant Type | Tissue Used |
|---|---|---|
| 1 | Wild type canola | Stem |
| 2 | Wild type canola | Leaves |
| 3 | Transgenic canola | Stem |
| 4 | Transgenic canola | Leaves |
| 5 | Transgenic canola | Stem |
| 6 | Transgenic canola | Leaves |
| 7 | Willow | Stem with bark |
| 8 | Black Locust | Stem with bark |
| 9 | Burning Bush | Stem with bark |
| 10 | Poplar | Stem with bark |
| 11 | Poplar | Stem without bark |
| 12 | Cellulose paper | N/A |

*For convenience, treatments were labeled on Petri dish lids.

2.3 Experimental Setup

Replicated groups of 15 termite workers were weighted for initial body weight, before they were placed in a 35 cm Petri dish. To reduce stress, the bottom surface of each Petri dish was scratched using a utility knife to provide footing for termites. Testing materials were dried at 80° C. overnight and weighted. To examine the susceptibility of these testing materials to termites, they were used as the only food source (a "no choice" test). Materials were soaked in distilled water for 1 hour before being introduced into the Petri dish. The bioassay were performed in complete darkness at 27±1° C. and 80±1% relative humidity, for 10 days. A total of four technical replications were performed for each treatment in each colony (60 termites/treatment/colony).

2.4 Data Documentation

Mortality and body weight of termite workers were monitored throughout the experiment. Cumulative mortality at the 5th and 10th day, as well as the body weight of survived workers at the 10th day were documented. Mortality data at day-5 is reported for the experiments.

3. Results 3.1 Transgenic Lines of Canola

Figure 10:
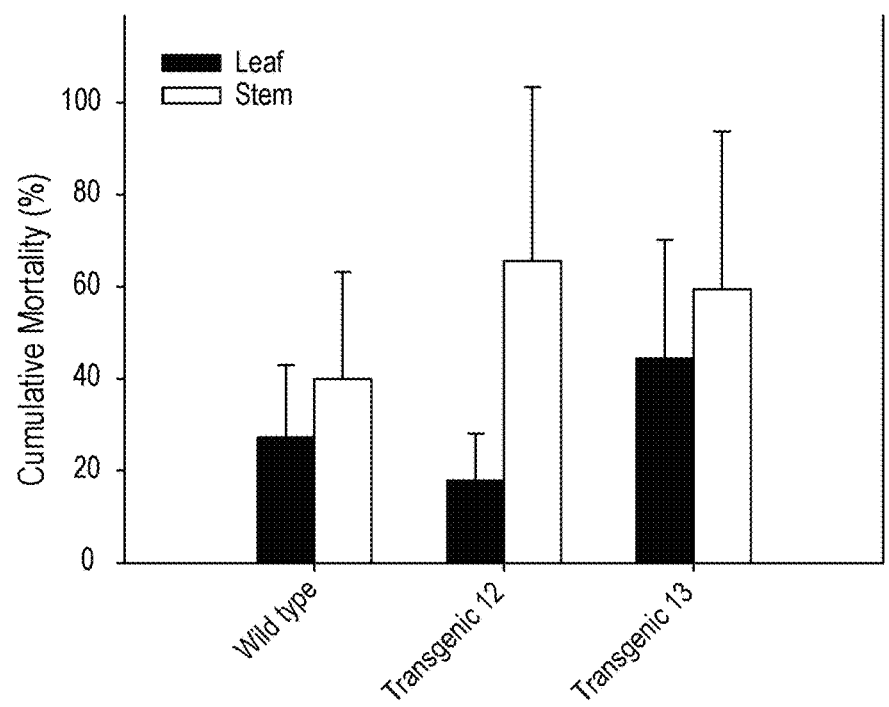
FIG. 10 is a graph showing the mortality of termite populations following exposure to wild type leaves and stems from canola, and exposure to transgenic leaves and stems from canola.

Referring to FIG. 10, in general, termites that fed on transgenic canola, including leaves and stems, exhibited higher mortality than their wild type counterparts, (with the exception of leaves from transgenic line 12).

3.2 Different Type of Woody Materials

Figure 11:
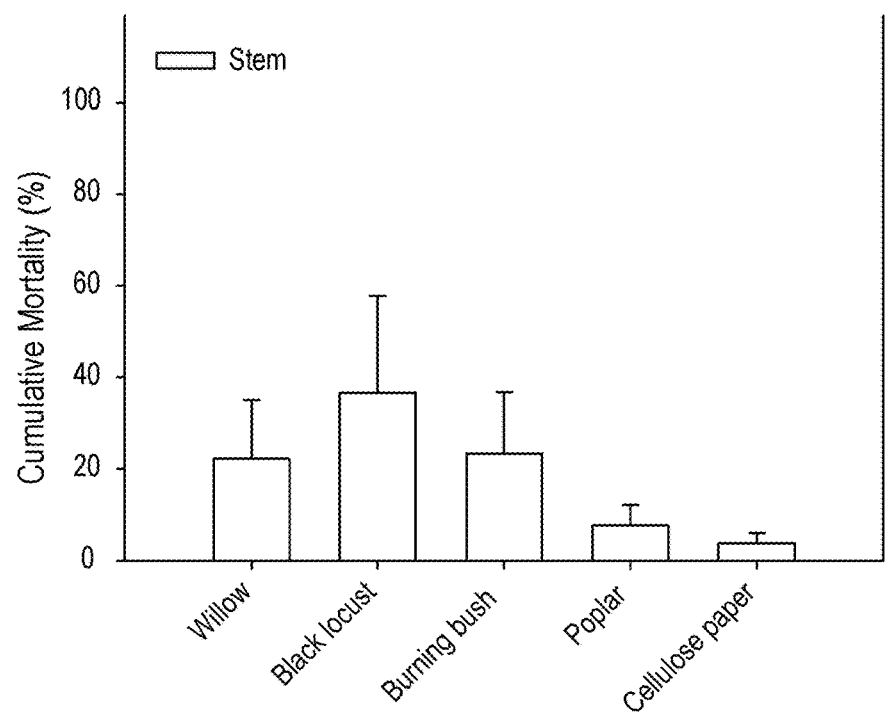
FIG. 11 is a graph showing the mortality of termite populations following exposure to multiple types of woody materials.

Referring to FIG. 11, termites that fed on black locust displayed the highest mortality among the woody materials tested in this experiment. Cellulose paper, as expected, had the lowest mortality (5%) at day-5. As described above, a gene construct including 3 black locust genes was used to create transgenic lines 12 and 13 used in this Example (and other Examples).

3.3 Woody Materials with or without Bark

Figure 12:
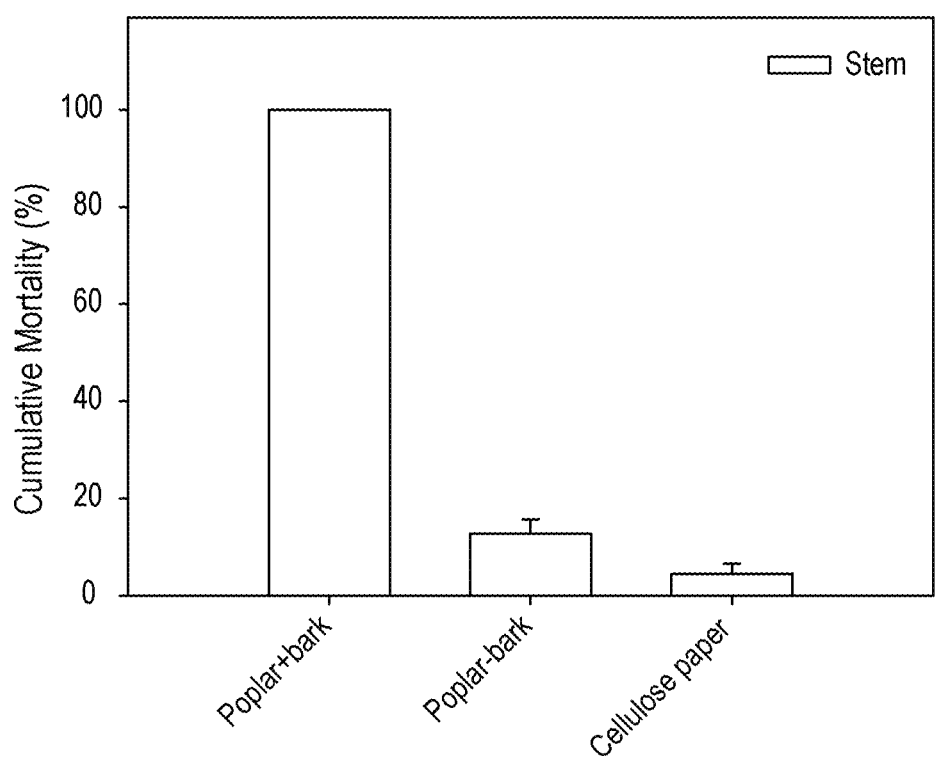
FIG. 12 is another graph showing the mortality of termite populations following exposure to multiple types of woody materials.

Referring to FIG. 12, without bark, poplar and cellulose paper were extremely susceptible to termite feeding, i.e., they are the best food source for termites (mortality level at approximately 10%). With bark, however, termites were dead completely at day-5 (FIG. 12).

3.4 Effects of Testing Materials on Termite Body Weight

Termite workers exhibited significant weight reduction after treatment, except groups treated with poplar (stem without bark) and paper. Groups fed with transgenic canola leaves exhibit higher weight reduction than do groups fed with wild type canola leaves. The transgenic line 12 treated group exhibited highest weight reduction among other treatment groups.

4. Discussion 4.1 Transgenic Lines of Canola

In comparison to the wild-type canola, transgenic canola has lethal (greater mortality) and sublethal (body weight loss) effects on termites given no choice of food. Two plausible mechanisms are the 1) direct toxicity and 2) reduced feeding caused by the expression of inserted genes in the transgenic lines.

4.2 Different Type of Woody Materials

Black locust is the least susceptible woody materials toward termite infestation.

4.3 Summary

The transgenic plants developed here can be potentially effective against termite infestation. And black locust (the source of the transgene construct) is relatively resistant to termite attack.

While the various aspects of the present invention have been disclosed by reference to the details of various embodiments of the invention, it is to be understood that the disclosure is intended as an illustrative rather than in a limiting sense, as it is contemplated that modifications will readily occur to those skilled in the art, within the spirit of the invention and the scope of any claims that appear in this or any subsequent application.

What is claimed is:

1. A transgenic plant comprising within its genome at least one transgene that, when expressed, provides resistance to an insect and/or a fungus;

wherein the at least one transgene comprises a cDNA encoding SEQ ID NO: 2, which is lectin polypeptide A of *Robinia pseudoacacia* bark agglutinin I ("LECRPA1"), a cDNA encoding SEQ ID NO: 4, which is lectin polypeptide B of *R. pseudoacacia* bark aqqlutinin I ("LECRPA2"), and a cDNA encoding SEQ II) NO: 6, which is lectin polypeptide C of *R. pseudoacacia* bark aqqlutinin II ("LECRPA3"), wherein the at least one transgene is operably linked to a promoter; and wherein the at least one transgene further encodes a Rubisco small subunit transit peptide operably linked to SEQ ID NO: 2, 4, and 6.

2. The transgenic plant of claim 1, wherein the nucleotide sequence of LECRPA1 cDNA comprises SEQ ID NO: 1.

3. The transgenic plant of claim 1, wherein the promoter is chosen from an Alfalfa RbcS gene promoter and a CaMV 35S promoter.

4. The transgenic plant of claim 3, wherein the promoter is an Alfalfa RbcS gene promoter, and has the sequence of SEQ ID NO: 7.

5. The transgenic plant of claim 1, wherein the Rubisco small subunit transit peptide has the sequence chosen from SEQ ID NO: 9.

6. The transgenic plant of claim 1, wherein the insect is a termite.

7. The transgenic plant of claim 1, wherein the fungus is chosen from *Phanerochaete chrysosporium, Gloeophyllum trabeum*, and *Trichoderma reesei*.

8. A fruit or a seed of the transgenic plant of claim 1, wherein the fruit or seed comprises the at least one transgene.

9. A transgenic plant comprising within its genome at least one transgene that, when expressed, provides resistance to an insect and/or a fungus;

wherein the at least one transgene comprises a cDNA encoding SEQ ID NO: 2, which is lectin polypeptide A of *Robinia pseudoacacia* bark agglutinin I ("LECRPA1"), a cDNA encoding SEQ ID NO: 4, which is lectin polypeptide B of *R. pseudoacacia* bark aqqlutinin I ("LECRPA2"), and a cDNA encoding SEQ ID NO: 6, which is lectin polypeptide C of *R. pseudoacacia* bark aqqlutinin II ("LECRPA3"), wherein the at least one transgene further encodes a Rubisco small subunit transit peptide operably linked to SEQ ID NO: 2, 4 and 6; and wherein the at least one transgene is operably linked to an Alfalfa RbcS gene promoter having the sequence of SEQ ID NO: 7.

10. The transgenic plant of claim 9, wherein the Rubisco small subunit transit peptide having the sequence of SEQ ID NO: 9.

* * * * *

UNITED STATES PATENT AND TRADEMARK OFFICE
CERTIFICATE OF CORRECTION

PATENT NO. : 10,316,327 B2
APPLICATION NO. : 14/212380
DATED : June 11, 2019
INVENTOR(S) : Yi Li et al.

Page 1 of 2

It is certified that error appears in the above-identified patent and that said Letters Patent is hereby corrected as shown below:

In the Drawings

FIG. 9, "Rotted/Rooting" should be --Rotted/Rotting--.

In the Specification

Column 3, Lines approx. 45-46, "FIG. 9 is a photograph showing detached leaves from one transgenic plant lines and" should be --FIG. 9 is a photograph showing detached leaves from one transgenic plant line and--.

Column 6, Line approx. 32, "to the one determined for the a polypeptide of RPbAI." should be --to the one determined for a polypeptide of RPbAI.--.

Column 9, Line approx. 35, "from the group comprising of promoters and terminators." should be --from the group comprising promoters and terminators.--.

Column 12, Lines approx. 9-10, "For example, the term "variants thereof" or refers to a polynucleotide sequence having" should be --For example, the term "variants thereof" refers to a polynucleotide sequence having--.

Column 18, Line approx. 52, "5X cDNA systhesis buffer" should be --5X cDNA synthesis buffer--.

In the Claims

Column 36, Line 63 (after Sequence), Claim 1, "aqqlutinin I ("LECRPA2"), and a cDNA" should be --agglutinin I ("LECRPA2"), and a cDNA--.

Column 36, Line 64 (after Sequence), Claim 1, "II) NO: 6, which is lectin" should be --ID NO: 6, which is lectin--.

Signed and Sealed this
Twenty-second Day of October, 2019

Andrei Iancu
*Director of the United States Patent and Trademark Office*

Column 36, Lines 64-65 (after Sequence), Claim 1, "*pseudoacacia* bark aqqlutinin II" should be --*pse-doacacia* bark agglutinin II--.

Column 38, Line 9, Claim 9, "aqqlutinin I ("LECRPA2"), and a cDNA" should be --agglutinin I ("LECRPA2"), and a cDNA--.

Column 38, Line 11, Claim 9, "*pseudoacacia* bark aqqlutinin II" should be --*pseudoacacia* bark agglutinin II--.

Column 38, Lines 18-20, Claim 10, "The transgenic plant of claim 9, wherein the Rubisco small subunit transit peptide having the sequence of SEQ. ID NO: 9." should be --The transgenic plant of claim 9, wherein the Rubisco small subunit transit peptide has the sequence of SEQ. ID NO: 9.--.

SEQUENCE LISTING

```
<160> NUMBER OF SEQ ID NOS: 19

<210> SEQ ID NO 1
<211> LENGTH: 858
<212> TYPE: DNA
<213> ORGANISM: Robinia pseudoacacia

<400> SEQUENCE: 1
atgacttcct acaacttcaa aacccaaacc tccttccctc ttctcctatc catatccttt      60
tttttcctct tgttactcaa caaggtgaat tcaactggat ctctctcctt ttctttcccc     120
aagttcgcgc ctaaccaacc atatctgatc ttccaacgtg atgcccttgt gacatcaaca     180
ggggtgttac aactcaccaa cgtagttaac gggtaccat ccggtaaatc tcttggtaga     240
gctctatatg ctgccccttt ccaaatctgg gatagcacca caggcaacgt ggctagcttt     300
gtcacttcct tctcctttat cattcaagca cctaacccaa ccacaacggc agatggtctt     360
gccttctttc ttgcaccagt tgatactcag cccttagatg ttggaggaat gctcggaatt     420
ttcaaagacg gatatttcaa taaatccaac caaattgttg cagttgaatt cgatacctt    480 tcaaatattc actttgatcc aaaaggtaga catatgggaa tcaatgtcaa ctccatcgtg     540
tccataaaaa ccgtgccatg gaattggaca aatggcgaag tagccaatgt tttcataagc     600
tatgaagctt ccaccaaatc cttaactgcc tcttggttt atcctcact tgaaacaagt     660 tttatcgttc atgctattgt ggatgtgaag gatgttcttc ccgagtgggt aagatttggt     720
ttctcagcta ccacaggaat agataaaggc tacgttcaaa caatgatgt tctctcctgg     780 tctttcgagt caaacttgcc aggtggtaac agtgttgctt cggtgaagaa cgcgggtctt     840
tcaacctatg ctgcatga                                                  858

<210> SEQ ID NO 2
<211> LENGTH: 285
<212> TYPE: PRT
<213> ORGANISM: Robinia pseudoacacia

<400> SEQUENCE: 2

Met Thr Ser Tyr Asn Phe Lys Thr Gln Thr Ser Phe Pro Leu Leu Leu
1               5                   10                  15

Ser Ile Ser Phe Phe Phe Leu Leu Leu Asn Lys Val Asn Ser Thr
                20                  25                  30

Gly Ser Leu Ser Phe Ser Phe Pro Lys Phe Ala Pro Asn Gln Pro Tyr
            35                  40                  45

Leu Ile Phe Gln Arg Asp Ala Leu Val Thr Ser Thr Gly Val Leu Gln
        50                  55                  60

Leu Thr Asn Val Val Asn Gly Val Pro Ser Gly Lys Ser Leu Gly Arg
```

```
             65                  70                  75                  80
Ala Leu Tyr Ala Ala Pro Phe Gln Ile Trp Asp Ser Thr Thr Gly Asn
                    85                  90                  95

Val Ala Ser Phe Val Thr Ser Phe Ser Phe Ile Ile Gln Ala Pro Asn
                    100                 105                 110

Pro Thr Thr Thr Ala Asp Gly Leu Ala Phe Phe Leu Ala Pro Val Asp
                    115                 120                 125

Thr Gln Pro Leu Asp Val Gly Gly Met Leu Gly Ile Phe Lys Asp Gly
            130                 135                 140

Tyr Phe Asn Lys Ser Asn Gln Ile Val Ala Val Glu Phe Asp Thr Phe
145                 150                 155                 160

Ser Asn Ile His Phe Asp Pro Lys Gly Arg His Met Gly Ile Asn Val
                    165                 170                 175

Asn Ser Ile Val Ser Ile Lys Thr Val Pro Trp Asn Trp Thr Asn Gly
                    180                 185                 190

Glu Val Ala Asn Val Phe Ile Ser Tyr Glu Ala Ser Thr Lys Ser Leu
                    195                 200                 205

Thr Ala Ser Leu Val Tyr Pro Ser Leu Glu Thr Ser Phe Ile Val His
            210                 215                 220

Ala Ile Val Asp Val Lys Asp Val Leu Pro Glu Trp Val Arg Phe Gly
225                 230                 235                 240

Phe Ser Ala Thr Thr Gly Ile Asp Lys Gly Tyr Val Gln Thr Asn Asp
                    245                 250                 255

Val Leu Ser Trp Ser Phe Glu Ser Asn Leu Pro Gly Gly Asn Ser Val
                    260                 265                 270

Ala Ser Val Lys Asn Ala Gly Leu Ser Thr Tyr Ala Ala
                    275                 280                 285

<210> SEQ ID NO 3
<211> LENGTH: 861
<212> TYPE: DNA
<213> ORGANISM: Robinia pseudoacacia

<400> SEQUENCE: 3
atggcttcct acaagttcaa aacccaaaac tccttccttc ttctcctatc catatccttt      60
ttcttcctct tgttactcaa caaggtgaat tcgactggat ccctctcctt ttctttcccc     120
aagttcaagc atagccaacc agatctgatc ttccaaagtg atgcccttgt gacatcaaaa     180
ggggtgttac aactcaccac ggtaaatgat ggaagaccag tctatgactc tattggtcga     240
gttctatatg ctgccccttt ccaaatttgg gatagcacca ctggcaacgt ggctagcttt     300
gtcacttcct tctcctttat catcaaagca cctaacgaag caaaacggc agatggtctt      360 gtcttctttc ttgcaccagt tggtagtact cagcccctaa aggaggagg actcctcgga      420 cttttcaaag atgaatctta caataaatcc aaccaaattg ttgcagttga atttgacaca     480
tttcggaatg ttgcatggga tccaaatgga atacatatgg gaatcgatgt caactctatt     540
caatccgtaa gaactgtgcg atgggattgg gcgaatggcg aagtagccaa tgttttcata     600
agctatgaag cttccaccaa atccttaact gcctctttgg tttatccttc acttgaaaaa     660
agttttatct tgagtgctat tgtggatttg aagaaagttc ttccggagtg ggtaagagtt     720
ggtttcacag ctaccacagg actatctgaa gactacgttc aaacaaatga tgttctctcc     780
tggtctttcg agtcaaactt gccaggtggt aacagtgttg cttcggtgaa gaacgcgggt     840 cttttcaacct atgctgcatg a                                              861
```

<210> SEQ ID NO 4
<211> LENGTH: 286
<212> TYPE: PRT
<213> ORGANISM: Robinia pseudoacacia

<400> SEQUENCE: 4

Met Ala Ser Tyr Lys Phe Lys Thr Gln Asn Ser Phe Leu Leu Leu Leu
1               5                   10                  15

Ser Ile Ser Phe Phe Phe Leu Leu Leu Asn Lys Val Asn Ser Thr
            20                  25                  30

Gly Ser Leu Ser Phe Ser Phe Pro Lys Phe Lys His Ser Gln Pro Asp
            35                  40                  45

Leu Ile Phe Gln Ser Asp Ala Leu Val Thr Ser Lys Gly Val Leu Gln
50                  55                  60

Leu Thr Thr Val Asn Asp Gly Arg Pro Val Tyr Asp Ser Ile Gly Arg
65                  70                  75                  80

Val Leu Tyr Ala Ala Pro Phe Gln Ile Trp Asp Ser Thr Thr Gly Asn
                85                  90                  95

Val Ala Ser Phe Val Thr Ser Phe Ser Phe Ile Ile Lys Ala Pro Asn
            100                 105                 110

Glu Gly Lys Thr Ala Asp Gly Leu Val Phe Phe Leu Ala Pro Val Gly
            115                 120                 125

Ser Thr Gln Pro Leu Lys Gly Gly Leu Leu Gly Leu Phe Lys Asp
            130                 135                 140

Glu Ser Tyr Asn Lys Ser Asn Gln Ile Val Ala Val Glu Phe Asp Thr
145                 150                 155                 160

Phe Arg Asn Val Ala Trp Asp Pro Asn Gly Ile His Met Gly Ile Asp
                165                 170                 175

Val Asn Ser Ile Gln Ser Val Arg Thr Val Arg Trp Asp Trp Ala Asn
            180                 185                 190

Gly Glu Val Ala Asn Val Phe Ile Ser Tyr Glu Ala Ser Thr Lys Ser
            195                 200                 205

Leu Thr Ala Ser Leu Val Tyr Pro Ser Leu Glu Lys Ser Phe Ile Leu
210                 215                 220

Ser Ala Ile Val Asp Leu Lys Lys Val Leu Pro Glu Trp Val Arg Val
225                 230                 235                 240

Gly Phe Thr Ala Thr Thr Gly Leu Ser Glu Asp Tyr Val Gln Thr Asn
                245                 250                 255

Asp Val Leu Ser Trp Ser Phe Glu Ser Asn Leu Pro Gly Gly Asn Ser
            260                 265                 270

Val Ala Ser Val Lys Asn Ala Gly Leu Ser Thr Tyr Ala Ala
            275                 280                 285

<210> SEQ ID NO 5
<211> LENGTH: 783
<212> TYPE: DNA
<213> ORGANISM: Robinia pseudoacacia

<400> SEQUENCE: 5
atgctcataa gtttctttgt cttgctagct agtgccagaa aggagaactc tgatgaagga      60
atttccttca acttcaccaa cttcaccaga ggtgatcaag gtgtaacctt actaggacaa     120
gccaacatta tggcaaatgg gatcttggcc ctcaccaacc atacaaaccc tacttggaat     180
acaggccgtg ccttgtattc taaaccagtt cctatttggg attcagccac tggcaatgtc     240
gccagctttg ttacttcctt ctcttttgtc gtacaagaga tcaaggtgc tataccagct     300

```
gatggaattg ttttcttcct tgcaccagaa gccaggattc ccgacaattc agccggtggg    360
caactcggaa ttgttaatgc caacaaagct tacaatccat tgttggtgt agaatttgat     420 acttactcca ataattggga tcctaaatct gcacatattg gaatcgatgc cagctcttta   480
atttcattaa ggactgtgaa atggaacaag gttagtgggt cattggtcaa agttagtatc   540
atctatgact ctctatctaa gacgttgagt gttgttgtga ctcacgagaa tggtcaaatt   600
tctaccatcg ctcaagtcgt ggatttgaaa gctgtgctgg gagagaaggt cagggttggt   660
tttactgcag ccaccacaac aggccgggaa ttatacgaca ttcatgcatg gtctttcact   720
tcaactttgg tgacagctac aagcagcacc tcgaagaaca tgaatattgc aagctatgca   780
tga                                                                  783
```

```
<210> SEQ ID NO 6
<211> LENGTH: 260
<212> TYPE: PRT
<213> ORGANISM: Robinia pseudoacacia

<400> SEQUENCE: 6
```

```
Met Leu Ile Ser Phe Phe Val Leu Leu Ala Ser Ala Arg Lys Glu Asn
1               5                   10                  15

Ser Asp Glu Gly Ile Ser Phe Asn Phe Thr Asn Phe Thr Arg Gly Asp
            20                  25                  30

Gln Gly Val Thr Leu Leu Gly Gln Ala Asn Ile Met Ala Asn Gly Ile
        35                  40                  45

Leu Ala Leu Thr Asn His Thr Asn Pro Thr Trp Asn Thr Gly Arg Ala
50                  55                  60

Leu Tyr Ser Lys Pro Val Pro Ile Trp Asp Ser Ala Thr Gly Asn Val
65                  70                  75                  80

Ala Ser Phe Val Thr Ser Phe Ser Phe Val Val Gln Glu Ile Lys Gly
                85                  90                  95

Ala Ile Pro Ala Asp Gly Ile Val Phe Phe Leu Ala Pro Glu Ala Arg
            100                 105                 110

Ile Pro Asp Asn Ser Ala Gly Gly Gln Leu Gly Ile Val Asn Ala Asn
        115                 120                 125

Lys Ala Tyr Asn Pro Phe Val Gly Val Glu Phe Asp Thr Tyr Ser Asn
    130                 135                 140

Asn Trp Asp Pro Lys Ser Ala His Ile Gly Ile Asp Ala Ser Ser Leu
145                 150                 155                 160

Ile Ser Leu Arg Thr Val Lys Trp Asn Lys Val Ser Gly Ser Leu Val
                165                 170                 175

Lys Val Ser Ile Ile Tyr Asp Ser Leu Ser Lys Thr Leu Ser Val Val
            180                 185                 190

Val Thr His Glu Asn Gly Gln Ile Ser Thr Ile Ala Gln Val Val Asp
        195                 200                 205

Leu Lys Ala Val Leu Gly Glu Lys Val Arg Val Gly Phe Thr Ala Ala
    210                 215                 220

Thr Thr Thr Gly Arg Glu Leu Tyr Asp Ile His Ala Trp Ser Phe Thr
225                 230                 235                 240

Ser Thr Leu Val Thr Ala Thr Ser Ser Thr Ser Lys Asn Met Asn Ile
                245                 250                 255

Ala Ser Tyr Ala
            260
```

<210> SEQ ID NO 7
<211> LENGTH: 1828
<212> TYPE: DNA
<213> ORGANISM: Medicago sativa

<400> SEQUENCE: 7

```
tcgacctgca ggtcaacgga tcaaatgatt caatatttgg cttgatgaaa ttagagaaaa      60
tgaaaaattg gatttctaag tttgattgtt attttgagat agaaaaggaa aaatctctaa     120
tctcttacgc aagacctgcc tcaaccactt gataaactct tttgtctacg tattgaaaac     180
aaaagaggca ataaacatc tagccaaatg aaacaccaat aatgctttaa acaaaatgga      240
ataattgcat catcaattaa tctttataag tgagaatttt ccctcctata ataatgcgct     300
aggtatcaat tttcaactct gaaatataaa gcttcaagcg tgtgttatca aaaatcaagc     360
acagtaaaat cataagcaga atcattggtg atgctaatag ttgatgtgga atcgaacaat     420
gttcatattc tgataccttg ttggtgacaa gtcaagaccc ttatagactt gaattttgtc     480
tgagttgatg atttcagaag gggaatctag tatctaagta gatggtaaat ttattttttc     540
caattccagt tgcttccatt atgaacaaac cttattcttt taggctaata ttgaggaaca     600
aaagccacgg aatatttttt ttatgtataa cctaagaaaa agacaataat aaaaataatt     660
aaaaactaca acagatgatt ttggacttga atcgaattgg attaatctta tacatgttgt     720
cgataaggat actagttata tgaagaagag aatcaattga aactttatt gtgctatata     780
taatgattta tgatatatgg agagagggat ggcagaatat gcaagtttgg aatcaattct     840
ggacattcat ggagggcggg tttatcatcg tgggtgtggt agggtggct gaggttctag      900
ggctacccag tactttatg atgttgttgt agtattttga acaaatttgt ttttaatttt      960
tatgtttgaa tattgggttt gtaacatatg gataatttgt ttttaatttt atgttcgaaa    1020
attgtgttgt ttttgatcat tttcattaca atatttattt atttattcac gaatgcatgt    1080
ttatatcaac aaattatata atctgtatgt atcatagtga aaacaaactc tgttttttctt   1140
ttgatacctt tcagattata taatttgaaa tgtcataaaa cagtttagat tatataatct    1200
gaaatatgcg ttttttacac cacattttgc attttgtgag gtgtttgaca cttttcggat    1260
tatataagtc aaattatttt aagaagtttc ggattatata tctgaaacat atgtttaact    1320
gacacataca caaacatctc tagggtgatt tgtcttccaa tagttttat actgtttgga    1380
ttatataatc cgaatcaagg ttaagaaaaa attagggcgc tcgaaaacca aatagggtgg    1440
gaaaagtaat gaccaatatt gattacccta taaggagcca agcctgaaa aaagtaccat     1500
acatgattga tatttgtgga ggcattaata gtcacaaaac tacacgtggc aattttatat    1560
tggtggctaa tgataaggct agcacaaaaa tttccattcc tgtgtggttg atatggcagc    1620
aaagtttatc atattcacaa ccaacaaaat ggtattatga agcattacca caatttataa    1680
gaccataata ttggaaatag gaaaataaaa acattatata tagcaagttt gagtataagc    1740
tttgcaattc aagcagaagt acatcttact ttactagtga actaagtaag ggagaaaaaa    1800
aatggcttcc tctatgatgt cctcttca                                        1828
```

<210> SEQ ID NO 8
<211> LENGTH: 240
<212> TYPE: DNA
<213> ORGANISM: Medicago sativa

<400> SEQUENCE: 8

```
atggcttcct ctatgctctc ttccgctact atggttgcct ctccggctca ggccactatg      60
```

```
gtcgctcctt tcaacggact taagtcctcc gctgccttcc cagccacccg caaggctaac    120
aacgacatta cttccatcac aagcaacggc ggaagagtta actgcatgca ggtgtggcct    180
ccgattggaa agaagaagtt tgagactctc tcttaccttc ctgaccttac cgattccgaa    240
```

```
<210> SEQ ID NO 9
<211> LENGTH: 80
<212> TYPE: PRT
<213> ORGANISM: Medicago sativa

<400> SEQUENCE: 9
```

```
Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Gly Lys
    50                  55                  60

Lys Lys Phe Glu Thr Leu Ser Tyr Leu Pro Asp Leu Thr Asp Ser Glu
65                  70                  75                  80
```

```
<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
atgacttcct acaacttc                                                    18
```

```
<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
tcatgcagca taggttga                                                    18
```

```
<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
atggcttcct acaagttc                                                    18
```

```
<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
tcatgcagca taggttga                                                    18
```

```
<210> SEQ ID NO 14
```

-continued

<211> LENGTH: 19
<212> TYPE: DNA
<213> ORGANISM: Artificial Sequence
<220> FEATURE:
<223> OTHER INFORMATION: Primer

<400> SEQUENCE: 14
atgctcataa gtttctttg 19

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
tcatgcatag cttgcaat 18

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
caccaacttc accagaggtg 20

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
cacggcctgt attccaagta gg 22

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
gcatctgcct cgacatcttg a 21

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gacagcagca ccttggaaat g 21